US011439783B2

(12) United States Patent
Ellis

(10) Patent No.: US 11,439,783 B2
(45) Date of Patent: Sep. 13, 2022

(54) CUSHION FOR PATIENT INTERFACE DEVICE, BREATHING MASK WITH CUSHION, AND METHOD AND APPARATUS FOR SAME

(71) Applicant: Michael P Ellis, Milford, MI (US)

(72) Inventor: Michael P Ellis, Milford, MI (US)

(*) Notice: Subject to any disclaimer, the term of this patent is extended or adjusted under 35 U.S.C. 154(b) by 1154 days.

(21) Appl. No.: 15/276,770

(22) Filed: Sep. 26, 2016

(65) Prior Publication Data
US 2017/0049983 A1 Feb. 23, 2017

Related U.S. Application Data

(63) Continuation-in-part of application No. PCT/US2015/000041, filed on Mar. 26, 2015.
(Continued)

(51) Int. Cl.
*A61M 16/06* (2006.01)
*B32B 5/02* (2006.01)
(Continued)

(52) U.S. Cl.
CPC .... *A61M 16/0622* (2014.02); *A61M 16/0057* (2013.01); *A61M 16/06* (2013.01); *A61M 16/0666* (2013.01); *B29C 51/082* (2013.01); *B29C 51/14* (2013.01); *B29C 51/32* (2013.01); *B29C 70/345* (2013.01); *B32B 3/266* (2013.01); *B32B 3/28* (2013.01); *B32B 5/024* (2013.01); *B32B 5/026* (2013.01); *B32B 5/04* (2013.01); *B32B 5/22* (2013.01); *B32B 5/26* (2013.01); *B32B 25/042* (2013.01); *B32B 25/10* (2013.01); *B32B 25/20* (2013.01);
(Continued)

(58) Field of Classification Search
CPC .............. A61M 16/06; A61M 16/0605; A61M 16/0616; A61M 16/0622; A62B 18/00; A62B 18/02; A62B 7/00; A41D 13/11; A41D 13/1146
See application file for complete search history.

(56) References Cited

U.S. PATENT DOCUMENTS 2,931,356 A 4/1960 Schwartz
6,016,805 A 1/2000 Burns et al.
(Continued)

FOREIGN PATENT DOCUMENTS

AU 2015237279 2/2019
EP 2478925 A2 7/2012
(Continued)

*Primary Examiner* — Margaret M Luarca
(74) *Attorney, Agent, or Firm* — John L. Chiatalas

(57) ABSTRACT

A patient interface device and cushion for the device are respectively disclosed, for preferred CPAP and BiPAP breathing masks. The cushion has a composite structure with an open rounded polygonal profile defining a mask side layer and a slip-resistant fibrous patient side layer, with an intermediate barrier layer positioned between the first and second layers. The layers are integrally bonded together into a three-dimensional conformation defining a J-shaped cross section and an inboard patient side curl opening into an air chamber juxtaposed with one or more of the patient's airways. The body exhibits flexibility between about 4 and about 10 Taber Stiffness Units. Method and apparatus for making the cushion are further described.

41 Claims, 33 Drawing Sheets

Related U.S. Application Data

(60) Provisional application No. 61/967,747, filed on Mar. 26, 2014.

(51) Int. Cl.

| | | |
|---|---|---|
| *B32B 25/20* | (2006.01) | |
| *B32B 3/28* | (2006.01) | |
| *B32B 25/10* | (2006.01) | |
| *B32B 5/26* | (2006.01) | |
| *B29C 70/34* | (2006.01) | |
| *B32B 5/22* | (2006.01) | |
| *B32B 3/26* | (2006.01) | |
| *B32B 5/04* | (2006.01) | |
| *B32B 25/04* | (2006.01) | |
| *A61M 16/00* | (2006.01) | |
| *B29C 51/08* | (2006.01) | |
| *B29C 51/14* | (2006.01) | |
| *B29C 51/32* | (2006.01) | |
| *B29K 83/00* | (2006.01) | |
| *B29K 105/00* | (2006.01) | |
| *B29L 31/00* | (2006.01) | |

(52) U.S. Cl.
CPC .  *A61M 16/0616* (2014.02); *A61M 2205/0216* (2013.01); *A61M 2205/7536* (2013.01); *A61M 2207/10* (2013.01); *B29K 2083/00* (2013.01); *B29K 2105/256* (2013.01); *B29L 2031/753* (2013.01); *B32B 2274/00* (2013.01); *B32B 2307/546* (2013.01); *B32B 2307/56* (2013.01); *B32B 2307/7246* (2013.01); *B32B 2307/7265* (2013.01); *B32B 2307/744* (2013.01); *B32B 2535/00* (2013.01)

(56) References Cited

U.S. PATENT DOCUMENTS

| | | | |
|---|---|---|---|
| 6,152,137 | A | 11/2000 | Schwartz et al. |
| 6,634,358 | B2 | 10/2003 | Kwok et al. |
| 6,871,649 | B2 | 3/2005 | Kwok et al. |
| 7,640,933 | B1 | 1/2010 | Ho |
| 7,717,114 | B1 | 5/2010 | Lagli |
| 7,814,910 | B2 | 10/2010 | Pan et al. |
| 8,132,270 | B2 | 3/2012 | Lang et al. |
| 8,276,588 | B1 | 10/2012 | Connor |
| 8,839,788 | B2 | 9/2014 | Betz et al. |
| 2005/0199239 | A1 | 9/2005 | Lang et al. |
| 2009/0107507 | A1 | 4/2009 | Moore |
| 2009/0139525 | A1 | 6/2009 | Schirm |
| 2009/0293880 | A1 | 12/2009 | Rutan |
| 2010/0024811 | A1 | 2/2010 | Henry et al. |
| 2010/0031958 | A1 | 2/2010 | Stewart |
| 2011/0005524 | A1 | 1/2011 | Veliss et al. |
| 2011/0023882 | A1 | 2/2011 | Nickol et al. |
| 2011/0086208 | A1 | 4/2011 | Nemphos, Jr. et al. |
| 2011/0088698 | A1 | 4/2011 | Barnett et al. |
| 2012/0080035 | A1* | 4/2012 | Guney .............. A61M 16/0616 128/205.25 |
| 2012/0132208 | A1 | 5/2012 | Judson et al. |
| 2012/0204881 | A1 | 8/2012 | Davidson et al. |
| 2013/0199537 | A1* | 8/2013 | Formica ........... A61M 16/0622 128/205.25 |
| 2014/0158136 | A1* | 6/2014 | Romagnoli ....... A61M 16/0875 128/206.24 |
| 2014/0283832 | A1 | 9/2014 | Stegman |
| 2014/0326246 | A1 | 11/2014 | Chodkowski et al. |

FOREIGN PATENT DOCUMENTS

| | | |
|---|---|---|
| EP | 15768980.3 | 11/2016 |
| EP | 15768980.3-662 A2 | 2/2017 |
| EP | 15768980.3 | 12/2017 |
| EP | 15768980.3 | 1/2018 |
| EP | 15768980.3 | 2/2018 |
| JP | 2015012896 A2 | 1/2015 |
| JP | 2015012990 A2 | 1/2015 |
| WO | WO2013027144 A1 | 2/2013 |
| WO | WO2013084109 A1 | 6/2013 |
| WO | PCT2015000041 A2 | 7/2015 |
| WO | WO2015147947 A2 | 10/2015 |
| WO | WO2015147947 A3 | 9/2016 |

* cited by examiner

CUSHION FOR PATIENT INTERFACE DEVICE, BREATHING MASK WITH CUSHION, AND METHOD AND APPARATUS FOR SAME

RELATED APPLICATIONS

The subject matter of this application claims priority from Applicant's prior application number PCT/US2015/000041, which in turn is based upon the U.S. Provisional Ser. No. 61/967,747; the entire contents of the afore-mentioned documents are expressly incorporated by reference herein and relied upon.

TECHNICAL FIELD

The current invention relates generally to breathing masks, particularly to Continuous Positive Air Pressure (CPAP) masks and to hospital respiratory masks, and more particularly, to wearer interfaces and cushions therefor.

BACKGROUND

Ventilation interfaces requiring a cushioned seal with the face of a patient-wearer are used for various applications. One such situation involves current treatments for obstructive sleep apnea syndrome (commonly referred to as obstructive sleep apnea, sleep apnea syndrome, and/or sleep apnea), which are referred to herein as "sleep apnea" masks. Another such situation involves administration of oxygen in an ambulance and/or hospital, referred to herein as "oxygen" masks. The same sleep apnea mask is reused nightly for months in a row, by the same patient for whom it is prescribed. Oxygen mask interfaces, on the other hand, are often disposed of following a single use that may last from a few hours to several days. Sleep apnea masks are of generally modular construction, allowing disassembly and cleaning of the interface components to maintain these in a sanitary condition. Oxygen masks tend to be of unitary construction and come in sanitary packaging, such that the entire mask may be opened, used and then discarded when a fresh mask is desired. A patient may nevertheless wear serial oxygen masks for an extended period of time while being treated, i.e., even if these are regularly changed. The degree of positive air pressure provided by the ventilation interface varies, depending on the patient's needs and the situation. In sleep apnea masks there is a much higher pressure of air being delivered versus oxygen masks that primarily enhance the oxygen content of air through the nostrils and mouth. The same applies to the plastic tubes that often are inserted directly into the nostrils to enrich the oxygen content per volume of air breathed in by the patient. Therefore a need exists for both the sleep apnea and oxygen mask applications to provide a comfortable interface that delivers gas without significant leakage from the interface over extended periods of time, as will be addressed herein.

Sleep apnea is a medical condition that includes repeated, prolonged episodes of cessation of breathing during sleep. During a period of wakefulness, the muscles of the upper part of the throat passage of an individual normally keep the passage open, thereby permitting an adequate amount of oxygen to flow into the lungs. During sleep, the throat passage tends to narrow due to the relaxation of the muscles. In those individuals having a relatively normal-sized throat passage, the narrowed throat passage remains open enough to permit an adequate amount of oxygen to flow into the lungs during sleep. However, in those individuals having a relatively smaller-sized throat passage, the narrowed throat passage prohibits an adequate amount of oxygen from flowing into the lungs. Additionally, a nasal obstruction, such as a relatively large tongue, and/or certain shapes of the palate and/or the jaw of an individual, further prohibit an adequate amount of oxygen from flowing into the lungs.

An individual having the above-discussed conditions of sleep apnea can stop breathing for one or more prolonged periods of time (e.g., ten seconds or more). The prolonged periods of time during which breathing is stopped, also known as apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and depression.

Use of oxygen masks, as mentioned previously, may correspond to medical conditions other than sleep apnea. Such other conditions may also prevent individuals, including adults and infants, from receiving an adequate amount of oxygen into the lungs. For example, an infant who is born prematurely can have lungs that are not developed to an extent necessary to receive an adequate amount of oxygen. Further, prior to, during and/or subsequent to certain medical procedures and/or medical treatments, an individual can be unable to receive an adequate amount of oxygen. Oxygen masks are often used in these situations, where a patient typically is not moving the head as can happen otherwise during sleep. Institutional uses of such masks result in these being thrown away once worn by a particular patient, even changed intermittently for a given patient as mentioned above. It would not be economical or necessary to dispose of a more expensive sleep apnea mask interface in this environment, or even components of such a modular construction that alone can be relatively expensive. In comparison, a series of disposable oxygen masks could still, in many cases, need to be worn by an individual on an extended basis. That is, before and during hospitalization as well as on an outpatient basis, e.g., in the case of ambulatory use. Some patients wear plastic tubing in their nostrils to provide oxygen-rich air to the lungs, which can become irritating over time.

Under these circumstances, it is known to use a ventilation interface to apply a positive pressure to the throat of the individual, thereby permitting an adequate amount of oxygen to flow into the lungs. In known ventilation interfaces, oxygen-enriched air and/or room air containing oxygen is delivered through the mouth and/or nose of the individual.

There exist several types of positive pressure applied by the known ventilation interface options. With respect to sleep apnea masks, one type is continuous positive airway pressure (CPAP), in which a positive pressure is maintained in the throat passage throughout a respiratory cycle. Another type is bi-level positive airway pressure (BiPAP), in which a relatively high positive pressure is maintained during inspiration and a relatively low positive pressure is maintained during expiration. Yet another type is intermittent mechanical positive pressure ventilation (IPPV) in which a positive pressure is applied when apnea is sensed, i.e., the positive airway pressure is applied intermittently or non-continuously. These masks typically have a flexible seal adapted to be interposed immediately between a patient's face and the rigid structure of the mask, for preventing leakage of gas supplied to the patient.

Conventional ventilation interfaces of ventilation systems include nasal masks, full masks and nasal pillows, among others. For example, many nasal ventilation systems include a mask interface that fits over the nose and rests above the upper lip of a user. A full mask interface fits over both the nose and mouth, resting under the lower lip of the wearer. The immediately afore-mentioned masks are intended to provide a space of gas (e.g., air) for inhalation into the lungs for respiration. A further option is a type of nasal mask that does not cover the nose, rather utilizing a pair of frusto-conical nose "pillows" that fit within the nostrils, respectively. The above systems frequently suffer from gas leakage, creating an inability to assure ventilation in many users.

For example, some conventional masks incorporate a sealing surface that extends around the periphery of the mask. The sealing surface is often made of a highly flexible material that has been known to perform adequately when the fit happens to be good between the sealing surface and the corresponding contours of a particular wearer's face. When a user wears a mask a combination of variables affect the user's face-seal. It has been found that the human skin produces oils which affect the seal of a smooth or textured elastomeric cushion construction. The movement of the head during normal sleep and the production of the skin oils allow such masks to slide against the skin, creating a void or gas leak, particularly in the nose bridge area. Thus, allowing the gas to escape into the facial region of the eyes. This condition could wake the user, defeating the purpose of the mask by preventing a positive seal. This causes the user to tighten up the straps, causing considerable discomfort in this region of the face.

Nevertheless, some users will not experience an acceptable seal fit as gaps in the seal-to-face interface do occur. Often this is sought to be remedied by applying greater axial force to further compress the interface against a user's face, thereby attempting to seal where gaps have occurred. Many conventional ventilation systems use a headgear system having straps to bind the mask in place; the system is tightened to obtain a sufficient seal if one does not exist. The mask, headgear and/or individual straps thereby place greater pressure on the patient's face and/or head. Such straps can further compress uncomfortably about the head and ears when tightened. This often produces user discomfort even at places remote from the sealing surface, such as various types of skin irritation, particularly where the applied force exceeds the local perfusion pressure (i.e. the pressure that is sufficient to cut off surface blood flow).

Sealing problems causing discomfort are often exacerbated when the positive pressure of the gas being supplied is relatively high or is cyclical to high levels. The mask must be held against the face with a force sufficient to seal against leakage of the peak pressure of the supplied gas and as the gas pressure increases so does the needed force to prevent leakage. Overall, user discomfort must be taken into consideration as it may well cause discontinued cooperation with the treatment regimen.

PRIOR ART

One prior approach to patient comfort and sealing effectiveness has been to interpose a planar, i.e., two-dimensional flexible flap between the frame of a breathing mask and skin of a user's face, sometimes referred to as an "interface". In turn, this flap becomes compressed against the user's skin as the holding straps of the mask are tensioned. Application Publication No. US 2009/0107507, entitled "Forehead and Nose Bridge Pad for CPAP Interface", discloses a flap of flexible fabric, interposed between the skin of a user's forehead and the mask, with an additional flap of planar, flexible material positioned between the skin of the nose bridge and the mask. Application Publication No. US 2010/0031958, entitled "Respiratory Mask Interface", discloses a discrete hollow triangle shaped structure with planar layers of flexible material between which enclosures are defined containing a variety of fillings such as a cooling gel or padding. Application Publication No. US 2011/0005524, entitled "Pad for a Mask", uses a flat strip of flexible material between the mask and skin on the nose bridge of a user. In each of the three citations immediately above there is a normally flat, two-dimensional structure of flexible material that is normally non-shape-retaining, sandwiched between the mask and skin of a user's nose bridge. U.S. Pat. No. 6,016,805, entitled "Face Seal for a Respirator", discloses a welder's helmet and face shield with dual thin, flexible flaps of flat material that intersect under the chin of a wearer and are elasticized, for purposes of preventing noxious fumes from entering the mask under the chin while the user's head is being turned.

In another approach, a cushion for a CPAP mask has a hollow, generally triangular member with a thin silicone membrane extending into an opening to accommodate the wearer's nose. For example, U.S. Pat. No. 6,634,358, entitled "Nasal Mask Cushion Assembly", discloses such a cushion having an aperture for receiving the wearer's nose and a seal forming portion that is said to contact the crease between the sides of the nose and the face. U.S. Pat. No. 7,814,910, entitled "Nose Cap", proposes a hollow body nested within an outer covering, due to a telescoping relationship that further provides an air chamber that is said to provide comfort to the patient. The same complaints can come from patients on a ventilator in hospitals.

Yet another approach has been a surface treatment of material along the patient interface. For example, US2011/0023882, entitled "Surface Structure on Patient Interface", discloses a "scaly" silicone contact surface for a breathing mask. Differing topography levels alternately contact the skin and define air flow passages, respectively. U.S. Pat. No. 7,717,114, entitled "Mask Seal Interface", utilizes an elastomer containing precipitated particles on its surface, said to provide a ventilation interface for a CPAP mask. Similarly, U.S. Pat. No. 7,640,933, entitled "Hybrid Textured/Polished Respiratory Mask Seal and Respiratory Mask Using Same", discloses imparting a rough surface to the face seal either before or after the molding process, i.e., using either a photo-etched die or applying micro-particles on the molded seal.

Other approaches have sought to address the degree of flexibility of the cushion further toward sealing effectively against the skin. For example, US2005/0199239, entitled "Mask Cushioning and Forehead Pad for Respiratory Mask, Respiratory Mask in Addition to a Mould and Method for Their Production", discusses zones with an increased cross-section configured in the silicone mask cushioning to impart a shore hardness that differs from one region to another region. Similarly, US2010/0024811, entitled "Bladder Cushion, Forehead Cushion, Headgear Straps, headgear Cap and/or Chinstrap", shows a silicone cushion including two or more bladders arranged concentrically, each with a face-contacting portion. The bladders are independently pressurized for sealing in use.

The degree of application of the cushion against the face can depend upon the tautness of the straps of the mask around the head. Often where the straps are too tight in order to force the cushion further against the face, the bridge of the nose can be uncomfortably pinched against this area of the face. U.S. Pat. No. 8,132,270, entitled "Headband Device for an Oxygen Mask", proposes a dual headband strap arrangement including upper and lower band portions for applying a breathing mask. Even so, shortcomings of the cushion itself can still pose problems.

The afore-mentioned approaches of others insufficiently address the provision of a long-term engagement of the mask with the skin of a wearer, by forming a face-seal interface that keeps a more set shape and position to improve user comfort, particularly in C-PAP and BiPAP patient systems.

Prior nosepieces utilizing a flexible membranous portion that is, in effect, "plastered" against the skin, can be excessively pliable and discomfort can arise, as well as bothersome noise. More specifically, as the membranous lip of some nosepieces collapses, the silicone material can slide about on the face for lack of friction partially due to the natural skin oils. These movements cause the mask to shift such that the seal leaks, the mask loses pressure and an annoying flapping noise results (hence the term "flapper" that refers to the membranous portion) that can elicit complaints from the patient and those nearby.

There is a need for a face-seal made of resilient material comfortably conforming to a wearer's facial contours especially surrounding the nose (and in some cases the mouth), having sufficient resilience to return to its original, or at least substantially its original, shape upon removal from the wearer's face.

There is a further need for a respiratory mask that provides the immediately afore-mentioned face-seal The prior approaches, where applicable, have not been entirely successful and still have not fully met the need to provide a conforming nosepiece (C-PAP) and/or mouthpiece (BiPAP) that stays in place, and is comfortable throughout the period of use.

SUMMARY OF INVENTION AND ADVANTAGES

Therefore it is an object of the present invention to provide a cushion for a patient interface device, such as for a breathing mask, which is comfortable to wear while sealing air flow quietly and effectively inside such a mask.

It is another object of Applicant's invention to provide a soft, comfortable, cloth-like patient interface cushion that retains its shape and position, without impinging on the patient's facial contours, particularly the nose bridge.

It is yet another object of Applicant's invention to provide a seal made of a soft resilient material that can comfortably conform to the contours of a person's face especially surrounding the wearer's nose, having sufficient resilience to return to its original, or at least substantially its original, shape upon removal from the wearer's face.

It is still another object of Applicant's invention to counteract the oils emanating from human skin that allow filmy surfaces of existing interface devices to slide around during use.

Accordingly, in its various embodiments, the present invention provides novel products, processes and apparatus directed toward satisfying the above and other stated objects.

According to a product of the present invention, there is provided a cushion for a patient interface device and a device incorporating such cushion. The cushion is molded into a resilient three-dimensional anatomical shape, defining a contoured hollow body having a soft patient contacting portion and an interface coupling portion. The patient-contacting portion has an open, J-shaped cross section with an inboard curl leading to a dampening chamber that receives a dampening medium, e.g., ambient air or oxygen-enriched air. The patient contacting portion includes a fibrous, slip-resistant surface presented toward the patient's skin and a liquid impermeable barrier forming a secure seal with the patient's skin. The chamber is juxtaposed with one or more of the patient's airways and in fluid communication with an inlet that delivers a pressurized stream of the dampening medium. The body preferably exhibits flexibility between about 4 to about 10 Taber Stiffness Units. Again preferably, the body of the cushion is constructed of a stretch-bonded laminate including a discrete fibrous layer and a sealant layer deposited on the fibrous layer. Yet preferably, the cushion may take the form of a generally open triangular nosepiece adapted to seal around the patient's nose and rest against the upper lip, e.g., a CPAP or other, respiratory mask; alternatively, the cushion may be a generally open triangular shape adapted to seal around both the nose and mouth airways, resting against the lower lip, e.g., a BiPAP mask. Still preferably, the invention may take the form of a pair of generally open frusto-conical nose pillows projecting from a distribution chamber, such as an elongated regulator, or the pillows may have a modular construction with a separate pair of frusto-conical nasal cushions mounted on the pillows, respectively, such that the pillows may each form one-piece or two-piece constructions. In either case, the pillows (non-modular) or pillow-cushions (modular) have a fibrous skin contacting surface and a vapor impermeable barrier. A preferred inlet is tubular and projects from the distributor toward the patient with a terminal flare that partially supports the circular profile J-shaped inboard curl leading into the dampening chamber.

According to the present invention, apparatus is provided to make a cushion for a patient interface device, the cushion being of the type having a body with a patient-engaging portion and an interface-coupling portion. There is provided means for applying a sealant to a fabric, preferably an applicator and an application frame that holds the fabric taut as the sealant is applied, thus making a laminar composite. A mold assembly is provided including cavity and plug members with a retainer provided that is interposed between the members. The retainer preferably bears a ring that articulates with either of the cavity and plug, respectively. The retainer maintains the laminate in a fixed tensioned position as the cavity and plug close together on either side of the retainer to mold the laminate into a three-dimensional blank. Means are provided for trimming the blank into a finished body of the cushion. Preferably, one or more trim fixtures are included to trim the molded blank to form an inboard curl for the patient-engaging portion and an outboard interface-coupling portion, respectively. Preferably, there is an outer trim assembly for trimming the interface-coupling portion, and an inner trim fixture for trimming a J-shaped inboard curl of the patient-engaging portion. Preferably, the cavity and plug members have a complementary, generally open triangular depression and shaping contour, respectively, adapted to form the laminate into a blank from which the body is trimmed.

According to a method of the present invention, a cushion is made for a patient interface device. One step provides an applicator and an application fixture, holding a fibrous layer taut in the fixture while relatively moving the applicator and applying a biocompatible sealant to the fibrous layer. Preferably, the fibrous layer is held in a pre-stretched condition within the application fixture, as the applicator traverses the frame and deposits the sealant to be cured. Preferably, another stretch-bonded laminar composite is similarly formed of another fibrous layer and sealant, with both laminates being bonded together. Another general step provides a mold having a cavity and a plug, and positions the laminar composite in the mold between a cavity and plug, the mold being closed to form the composite into a three-dimensional blank corresponding to the mold contours. Preferably, the mold assembly includes a retainer that urges the laminar composite into a fixed position between the mold portions to form a blank. Another general step trims the blank to form a patient-engaging portion with a J-shaped inboard curl and yet another general step trims the blank to form an interface coupling portion having an outboard periphery, leaving a molded body that exhibits a Taber Stiffness Value between about 4 to about 10 Taber Stiffness Units. Preferably the mold contours are made to define a generally triangular or frusto-conical three-dimensional blank. More preferably, the blank is placed in an inner trim fixture having cavity and plug portions that close to form an inboard J-shaped curl in a patient-engaging portion of the blank. Also preferably, the blank is placed within an outer trim fixture having cavity and plug portions that close to form an outboard interface-coupling portion in the blank. Alternatively, the mold contours are preferably made to define a generally triangular or frusto-conical three-dimensional blank. Preferably, the blank is molded into a three dimensional, frusto-conical shape having an apical flare that forms a patient contacting J-shaped curl.

According to a first alternate embodiment of the product of the present invention, there is provided a cushion for a patient breathing mask interface, including a body with a slip-resistant patient engaging portion and an interface coupling portion. The body contains a first fibrous layer, a second fibrous layer superposed on the first layer, and a third, vapor impermeable barrier layer interposed between the first and second layers, the layers defining an open generally polygonal shape. A central aperture is formed through the layers, which are integrally bonded together into a laminar composite defining a form-fitting, generally self-adjusting three-dimensional body. The aperture forms an air chamber juxtaposed with one or more of the patient's airways and communicates with a pressurized air source. The body further has a J-shaped cross section including an inboard curl that engages the bridge of the patient's nose and his/her facial curves, and a contiguous outboard wall that terminates in a mask engaging rim. The laminar composite exhibits a Taber Stiffness Value between about 4 to about 10 Taber Stiffness Units. Preferably, at least one of the first and second layers is a fibrous material, which is more preferably a fleeced fabric having a knit surface and a puffy brushed surface, for example a sweatshirt fabric. It is further preferred that the second layer, which is closest the patient, has a puffy brushed surface that is in direct contact with the patient's skin, which leaves the knit surface juxtaposed with the elastomeric layer; alternatively, the puffy surface of the second layer may be juxtaposed with the elastomeric layer. It is also preferred that the first and second layers are each a fleeced fabric having a knit surface and a puffy brushed surface, with the knit surfaces of each layer being in direct contact with the elastomeric layer. It is also preferred that the cushion be part of a nosepiece for a Continuous Positive Air Pressure mask, covering the nasal airway of the patient. More preferably, the cushion covers airways of both the nose and mouth of the patient. Also preferably, the interface coupling portion is an outboard rim of the cushion is a flange that is adapted to engage a complementary structure provided on the mask.

According to a second alternate embodiment of the product of the present invention, there is provided a cushion for a Continuous Positive Air Pressure patient mask interface. The cushion has a first fibrous mask side layer, a second slip-resistant fibrous facial side layer, superposed on the first layer, and a third, elastomeric layer interposed between the first and second layers. The layers have an open, generally triangular shape with a central aperture, and are integrally bonded together into a laminar composite defining a form-fitting, generally self-adjusting three-dimensional triangular shaped body. The cushion has an air chamber juxtaposed with the patient's nasal airway and communicating with a pressurized air source that is external to the mask. The body has a J-shaped cross section including an inboard curl that engages the bridge of the patient's nose and facial contours and also including a contiguous outboard wall that terminates in a mask engaging rim. The laminar composite exhibits a Taber Stiffness Value between about 4 to about 10 Taber Stiffness Units.

According to a third alternate embodiment of the product of the present invention there is provided a nose pillow cushion for a Continuous Positive Air Pressure patient interface. The cushion has a first fibrous layer and a second fibrous layer superposed on the first layer, with a third, elastomeric sealant layer interposed between the first and second layers. The several layers are integrally bonded together into a three-dimensional laminar composite body defining a generally frustoconical hollow pillar. The aperture leads from the patient's nasal airway to an air chamber that communicates with a pressurized source external to the interface. The laminar composite exhibits a Taber Stiffness Value between about 4 to about 10 Taber Stiffness Units.

According to a first alternate embodiment of the method of the present invention there is provided a plurality of steps for making a breathing mask cushion. The method includes the steps of providing a mold having a male shaping member and a female cavity, providing first and second fibrous layers and providing a third, thermoplastic elastomer layer between the first and second fibrous layers. The layers are superposed with one another between the cavity and shaping member as the mold is closed. The mold is heated, curing the elastomer and bonding the fibrous layers together into a laminar composite exhibiting a Taber Stiffness Value between about 4 to about 10 Taber Stiffness Units. The mold is opened and the finished cushion removed. Preferably, a fabric having a knit surface and an opposite puffy brushed surface is provided as the second fibrous layer. More preferably, the elastomer is applied to the knit surface of the second layer. Also preferably, a knit surface and an opposite puffy brushed surface are provided as the first layer. More preferably, the elastomer is applied to the knit side of each of the first and second fibrous layers. Also more preferably, the elastomer is applied to the puffy brushed side of each of the first and second fibrous layers. Still preferably, a flowable, self-leveling silicone elastomer is applied to either of the first and second layers. More preferably, the flowable, self-leveling silicone elastomer is applied to either or both of the first and second layers. Again preferably, a spreadable silicone elastomer paste is applied to one or both of the first and second layers.

According to a second alternate embodiment of the method of the present invention there is provided a plurality of steps for making a cushion for a Continuous Positive Air Pressure mask. The method includes the steps of providing a mold having a male shaping member and a female cavity, providing a first fibrous layer and a second fibrous layer superposed on the first layer, each layer presenting a knit surface and a puffy brushed surface, stretching and holding at least one of the fibrous layers, applying a silicone elastomer to a surface of at least one fibrous layer, interposing the layers between the shaping member and cavity and closing the mold. The mold is heated, curing the elastomer and bonding the fibrous layers together into a laminar composite exhibiting a Taber Stiffness value between about 4 to about 10 Taber Stiffness Units. The mold is opened and a cushion blank is removed, then the blank is trimmed to define an outer periphery and an inner opening. Preferably, a flowable, self-leveling biocompatible silicone elastomer is applied to one or more of the fibrous layers. Alternatively, a spreadable biocompatible silicone elastomer paste is applied.

According to the present invention there is provided apparatus for producing a patient respiratory mask cushion. The apparatus includes a fixture for holding a fibrous sheet in a radially tensioned state, and an applicator for depositing a polymeric barrier material onto the sheet. Preferably, the applicator is movable relative to the fixture to deposit the barrier material onto the sheet. The apparatus further includes a mold with a female cavity member and a male shaping member having complementary contours, with the same fixture or a separate tambour fixture holding the tensioned sheet interposed between the shaping member and the cavity. The mold members are movable between open and closed positions to compress the tensioned sheet and induce it to assume the contours of a cushion body between the mating plug and cavity. Preferably, an inboard trim fixture mounts the molded body so that a provided punch may be passed through the body to form an opening that defines a J-curl of a body contacting portion for the cushion. Also preferably, an outboard trim fixture mounts the molded body and a press has a peripheral cutter that trims away excess material surrounding the body.

According to the present invention there is provided a patient interface for a Continuous Positive Air Pressure (CPAP) mask. The interface has a rigid shell with an external side having an inlet for a pressurized air source and an internal side with a support oriented toward the patient. The interface has a relatively flexible cushion with a body defining a support engaging portion and a patient-contacting portion opposite the support engaging portion. The patient contacting portion has a fibrous surface and a vapor barrier to seal against the patient's skin and prevent leakage of air from the interface. Preferably, a first fibrous layer is superposed on a second fibrous layer, with a third, preferably elastomeric, vapor barrier layer interposed between the first and second layers, the layers having a generally triangular shape. An aperture is formed through the layers, which are integrally bonded together into a laminar composite defining a form-fitting, generally self-adjusting three-dimensional shaped body with the aperture leading to an air chamber juxtaposed with the patient's nasal airway and communicating with the inlet. The body has a J-shaped cross section including an inboard curl that engages the bridge of the patient's nose and facial curves, and a contiguous outboard wall that terminates in a bracket engaging flange. The laminar composite exhibits a Taber Stiffness Value between about 4 to about 10 Taber Stiffness Units. Preferably, the cushion body is shape retaining without pinching at the patient's nose bridge. The cushion may have a modular construction, usable with a pre-form as a patient body side liner, or it may have an integral construction for use without a preform member.

According to the present invention there is provided an integral patient respiratory mask having a flexible cushion defining an inner wall and an outer wall, and a relatively rigid fluid impermeable shell. The shell has an outer periphery that is joined to the outer wall defining a dampening chamber between shell and cushion. The shell has an external side presenting an inlet for receiving a dampening medium, such as pressurized air, into the chamber, and an internal side presenting a support portion oriented toward the patient. The cushion has a body defining a support engaging portion and a patient-contacting portion opposite the support engaging portion. The patient contacting portion has a fibrous slip-resistant surface and a vapor barrier to seal against the patient's skin and prevent leakage of air therefrom. The patient contacting portion surrounds both the mouth and nose of the patient. Preferably, the body is a laminar composite exhibiting a Taber Stiffness Value between about 4 to about 10 Taber Stiffness Units. Also preferably, the shell is a molded plastic film, a fibrous web or a combination thereof.

An advantage of the present invention is a breathing mask cushion that retains its shape and size, even after repeated washings, resisting collapse when worn.

Another advantage of the present invention is a patient breathing mask interface having a slip-resistant cushion that correctly spaces the patient's nose from the mask, without excessive tightening of head straps that typically encircle the patient's head.

Yet another advantage of the present invention is a slip-resistant cushion for a breathing mask that maintains the mask in a fixed position on the patient's face during movement, particularly around the nasal airways.

Still another advantage of the present invention is a cushion that does not leak air, thus avoiding loud and unpleasant flapping noises.

Again another advantage of the present invention is a cushion that can be adapted for use as a liner fitting removably atop conventional silicone cushions that have lower flanges articulating with correspondingly shaped base A further advantage of the present invention is a method for making a patient breathing mask cushion that employs readily available materials and technologies, including apparatus for such manufacture.

The features and advantages of the disclosure will be set forth in the description which follows, and in part will be apparent from the description, or may be learned by practice of the disclosure without undue experimentation. The features and advantages of the disclosure may be realized and obtained by means of the devices and combinations particularly pointed out in the appended claims.

DETAILED DESCRIPTION OF THE FIGURES

Figure 1:
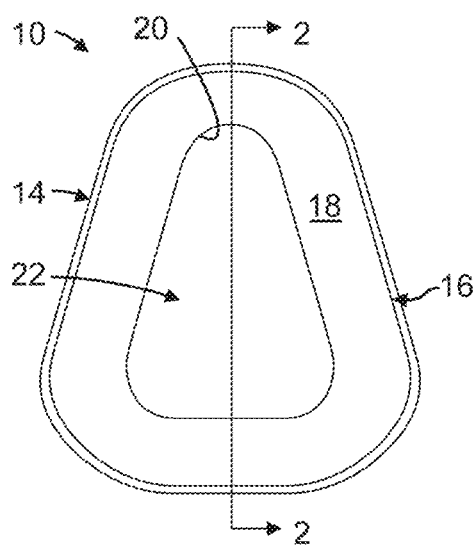
FIG. 1 is a top plan view of a face-seal cushion for a breathing mask interface showing an inboard patient-engaging curl and an outboard wall having a preferred flange for mounting the cushion on the interface, according to the present invention.
Figure 2:
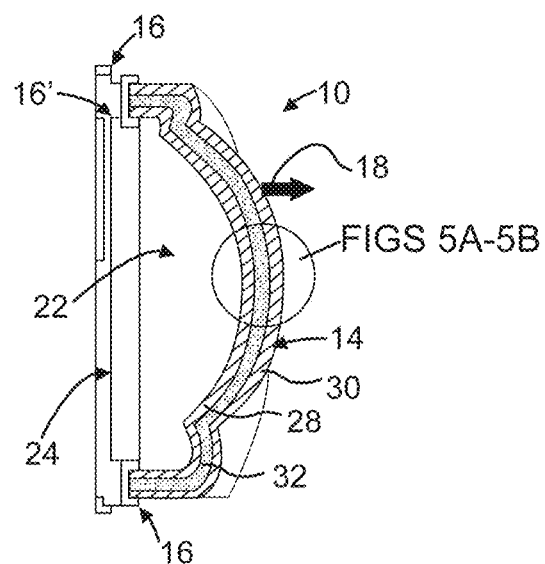
FIG. 2 is a sectional view taken along Lines 2-2 of FIG. 1, generally depicting the laminar composite material comprising the cushion of the present invention.
Figure 3:
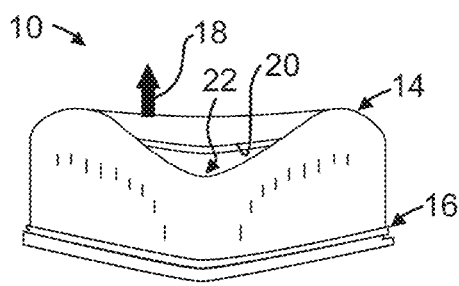
FIG. 3 is an elevational view of the cushion of FIGS. 1-2, showing the nose portion and lip curl of the cushion of the present invention, including the outboard wall with preferred mounting flange.
Figure 4:
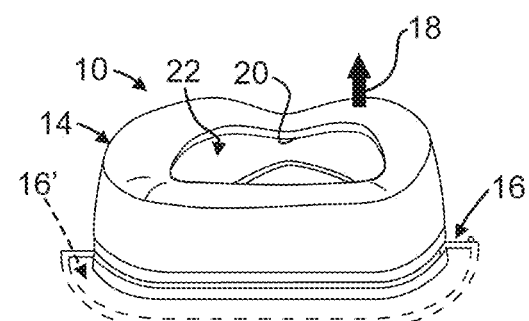
FIG. 4 is a perspective view of the cushion of FIGS. 1-3, showing the lip portion and nose curl of the cushion, including means for engaging the preferred mounting flange with the interface, according to the present invention.
Figure 5A:
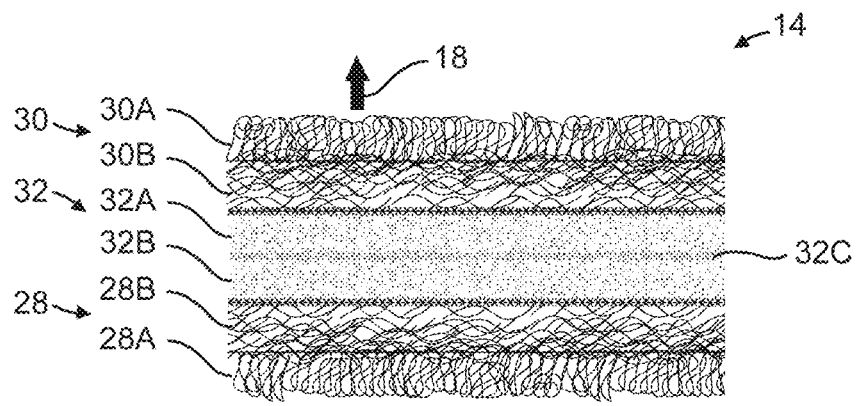
FIG. 5A is an enlarged view of the circular region delimited FIGS. 5A-5B in FIG. 2, showing a preferred laminar composite construction having dual layers of fleeced fabric wherein the loftier fleece side of each layer faces outwardly and the less lofty, smoother woven side faces inwardly, with a liquid impermeable barrier layer sandwiched between the juxtaposed woven sides, according to the present invention.
Figure 5B:
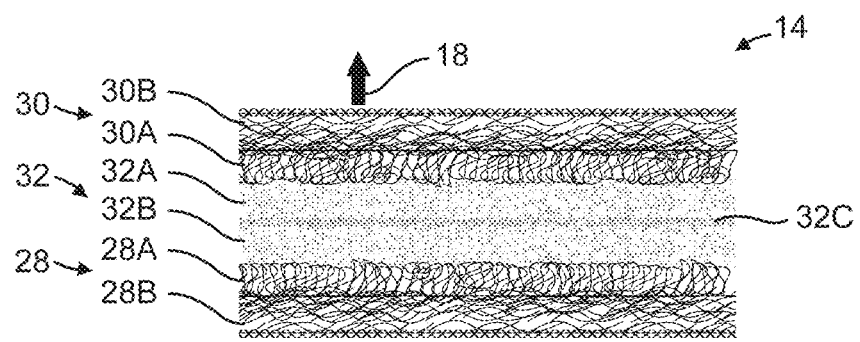
FIG. 5B is another enlarged view of the circular region delimited FIGS. 5A-5B in FIG. 2, showing an alternate preferred laminar composite construction having dual layers of fleeced fabric wherein the loftier fleece side of each layer faces inwardly and the less lofty/smoother woven side faces outwardly, with a liquid impermeable barrier layer sandwiched between the juxtaposed fleece sides, according to the present invention.
Figure 6:
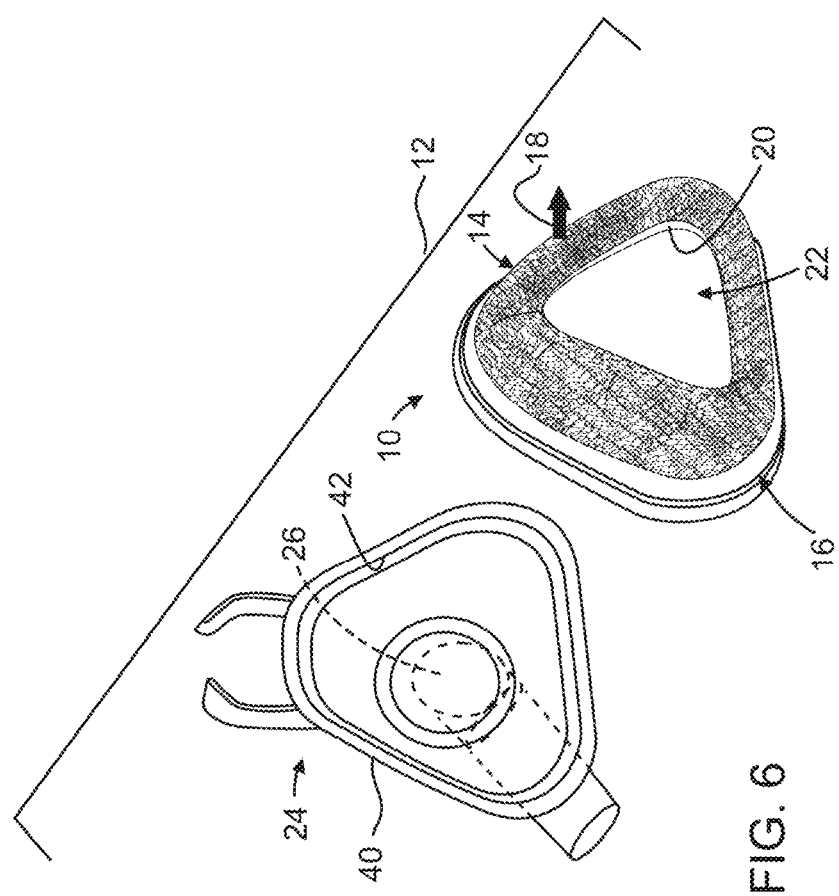
FIG. 6 is an exploded perspective view of a preferred interface for a breathing mask having a generally triangular shape surrounding the nose of a patient, including a shell having gas supply port, and a cushion such as in FIGS. 1-4 constructed of the composite of FIG. 5A or FIG. 5B, the cushion flange directly engaged with an outer periphery of the shell, without intermediate components, according to the present invention.
Figure 7:
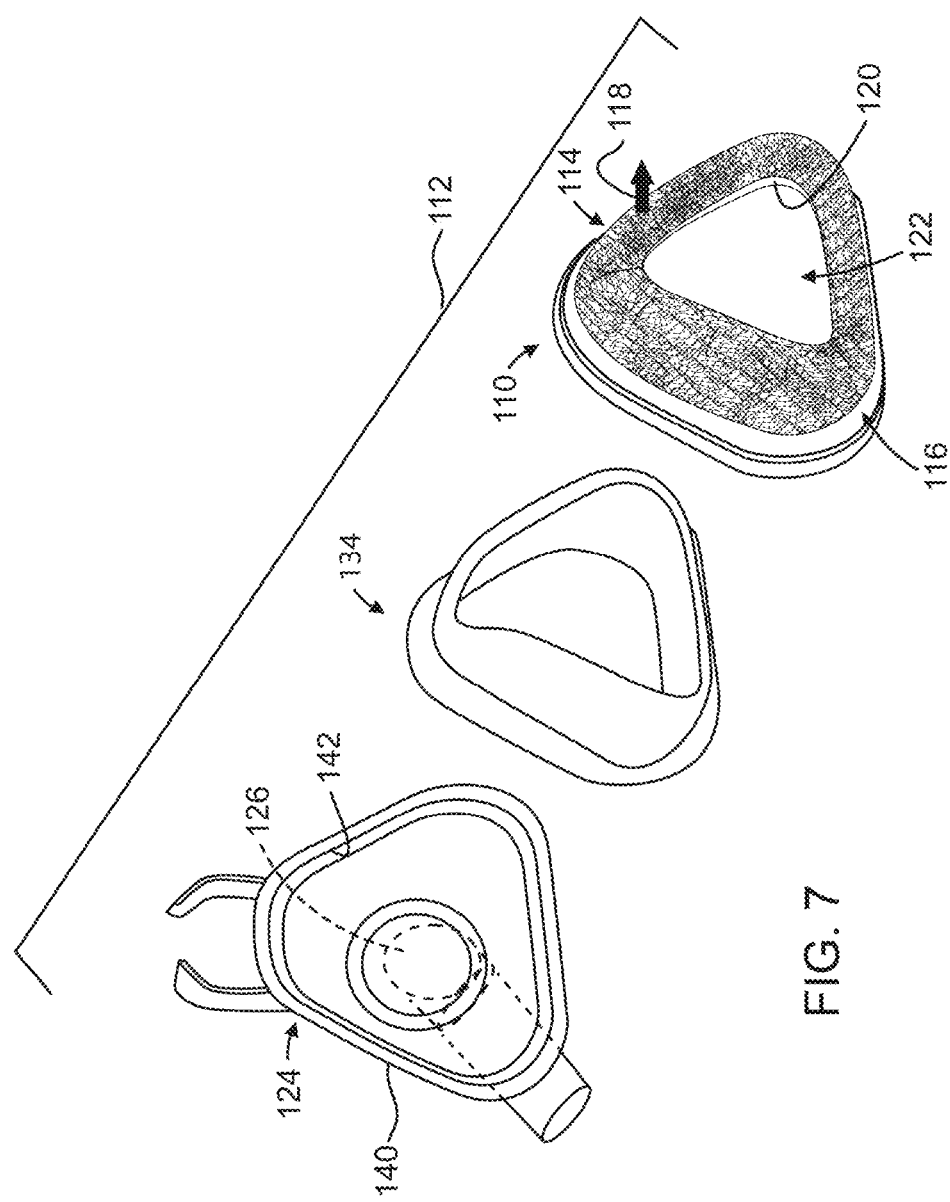
FIG. 7 is an exploded perspective view of an alternative interface for a breathing mask, including a shell and cushion surrounding the nose as in FIG. 6, with an intermediate preform engaging the shell and cushion, respectively, according to the present invention.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, any of the terms "embodiments of the invention", "embodiment" or "invention" does not require that all embodiments of the invention include the discussed feature, advantage or mode of operation.

Cushion embodiments can be designed as taught herein, to cooperate with nearly any ventilation interface that makes use of a cushion for sealing engagement with portions of a user's face. For examples, embodiments can be designed to cooperate with nasal masks, oral masks, full masks and portions of hybrid masks (i.e. those masks having an oral cavity and either nasal inserts or nasal prongs) of various styles and shapes as will be appreciated by those having ordinary skill in the art.

Nevertheless, for illustrative purpose and in a non-limiting fashion, at least one exemplary embodiment is described herein in reference to nasal masks, particularly nasal masks having a generally triangular portion adapted to mate (with or without additional mounting components) with a nasal cushion having a substantially triangularly-shaped (i.e. three-sided) frame that surrounds the nose and rests against the upper lip. At least another embodiment that is an alternative to the immediately preceding interface is a so-called "full mask" or Bi-PAP mask encompassing both mouth and nasal airways. Yet another alternative embodiment is a mask with dual frusto-conical cushions or "pillows" that project into the nostrils.

According to a product of the present invention, there is shown in FIGS. 1-9, 9A-9F and 10 a cushion 10, 110, 210, 310, 310', 410 for a patient breathing mask interface device, generally shown at 112, 212, 312, 312', 412 in FIGS. 6-9, 9A-9F and 10, respectively, the cushion having a three-dimensional molded body 14, 114, 214, 314, 314', 414, the body being form-fitting with an interface coupling portion generally indicated at 16, 116, 216, 316, 316', 416 and a patient contacting portion facing toward the wearer generally indicated by directional arrow 18, 118, 218, 318, 318', 418, the patient contacting portion having a J-shaped cross section defining an inboard curl 20, 120, 220, 320, 320', 420 opening into a dampening chamber 22, 122, 222, 322, 322', 422 located adjacent one or more of the patient's nasal and oral airways (not shown), the dampening chamber receiving a dampening medium, e.g., air, supplied to a mask shell generally shown at 24, 124, 224, 324, 324', 424 through an inlet 26, 126, 226, 326, 326', 426 that is in fluid communication with the chamber. Patient contacting portion 18, 118, 218, 318, 318', 418 is distinctively fibrous and slip-resistant with vapor barrier properties that maintain a sealing engagement of cushion 10, 110, 210, 310, 310', 410 against the patient's facial skin to keep air from leaking out of interface 12, 112, 212, 312, 312', 412. Body 14, 114, 214, 314, 314', 414 preferably exhibits flexibility between about 4 to about 10 Taber Stiffness Units as measured by the testing equipment of FIG. 40 and associated techniques and materials (FIG. 42) described herein, the body having a construction that will be appreciated by those skilled in the art from the ensuing description.

Composition of body 14, 114, 214, 314, 314', 414 is shown in exemplary detail by FIGS. 2, 5A-5B and FIGS. 10 and 10A-10B, preferably being a composite, more preferably a laminar and even more preferably a tri-laminar construction, these preferred constructions being enabled by a stretch-bonded lamination process described further herein. Included is a first layer 28, 428 closest to shell 24 and pillow 424, i.e., the mask side facing in a direction opposite arrows 18, 118, 218, 318, 318', 418. A second, slip-resistant fibrous layer 30, 430 presents a patient-contacting surface in the direction of arrow 18, 118, 218, 318, 318', 418 and superposed on first layer 28, 428, and a third layer of preferably elastomeric sealant 32, 432 which imparts the above-mentioned vapor barrier properties is interposed between the first and second layers. Body 14, 114, 214, 314, 314', 414 is preferably formed using a stretch-bonded lamination process alluded to previously, wherein fibrous second layer 30, 430 is held under tension while sealant layer 32, 432 is deposited on that tensioned fibrous second layer, the sealant being dried and/or cured thereon. More preferably first layer 28, 428 faces in a direction opposite from arrow 18, 118, 218, 318, 318', 418 toward shell 24 and pillow 424, the first layer also preferably being a fibrous material held in tensioned condition while another layer of the same or a different sealant 32, 432 is applied thereon, the two preferred fibrous layers 30, 430 and 28, 428, respectively, then being bonded to one another to form body 14, 114, 214, 314, 314', 414, as will be appreciated by those skilled in the art from Applicant's description herein.

In FIGS. 1-9 and FIGS. 9A-9E, body 14, 114, 214, 314, 314' is shown delimiting a, three-dimensional contour with an open, preferably polygonal and more preferably rounded triangular shape.

Figure 9:
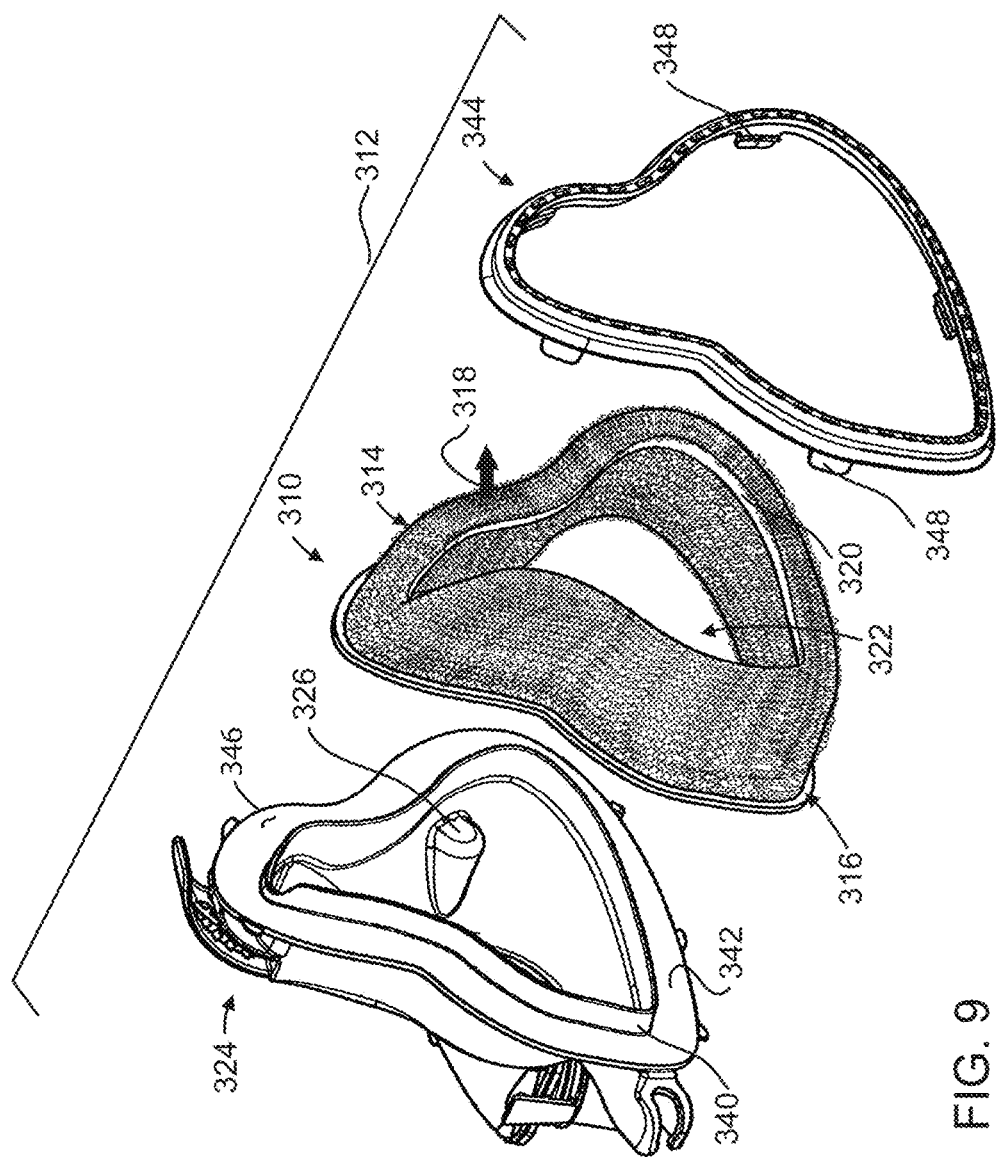
FIG. 9 is an exploded perspective view of an interface for a breathing mask, having a shell and a face seal cushion engaging the shell with a retaining frame snapped over the cushion onto the shell to retain the cushion in place surrounding the mouth and nose of a patient, according to the present invention.
Figure 9A:
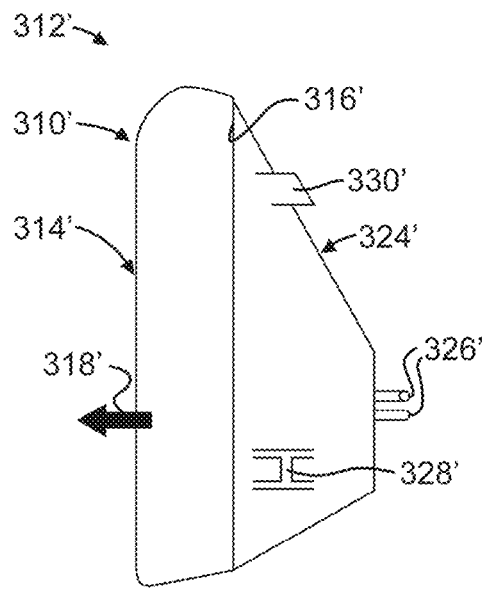
FIG. 9A is an elevational view of an alternative shape-retaining, slip-resistant face seal cushion similar to FIG. 9 in that the cushion surrounds both the mouth and nose of a patient, with the exception that the cushion is peripherally joined to a frontal shell to form an integral respiratory mask housing a dampening chamber between the cushion and shell, according to present invention.
Figure 9C:
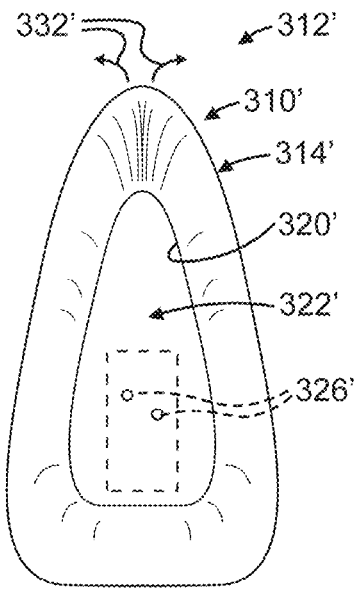
FIG. 9C is a back view of the respiratory mask of FIGS. 9A and 9B.
Figure 9B:
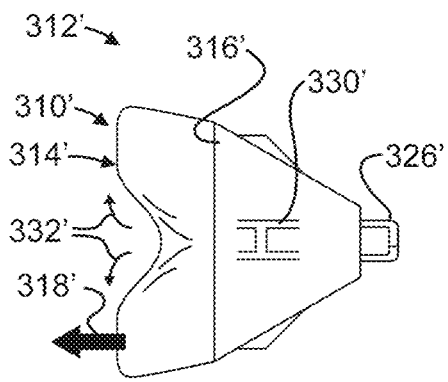
FIG. 9B is a top view of the respiratory mask of FIG. 9A.
Figure 9D:
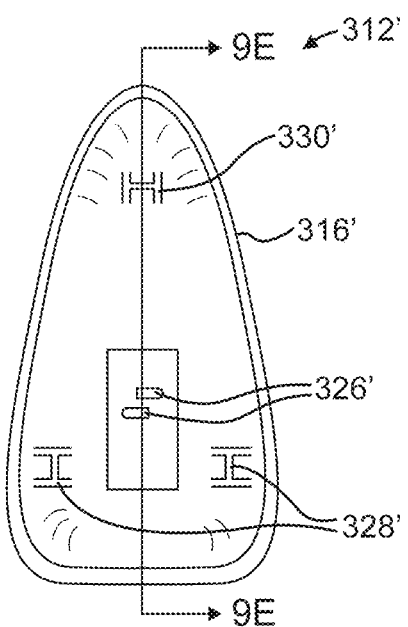
FIG. 9D is a front view of the respiratory mask of FIGS. 9A, 9B and 9C.
Figure 9E:
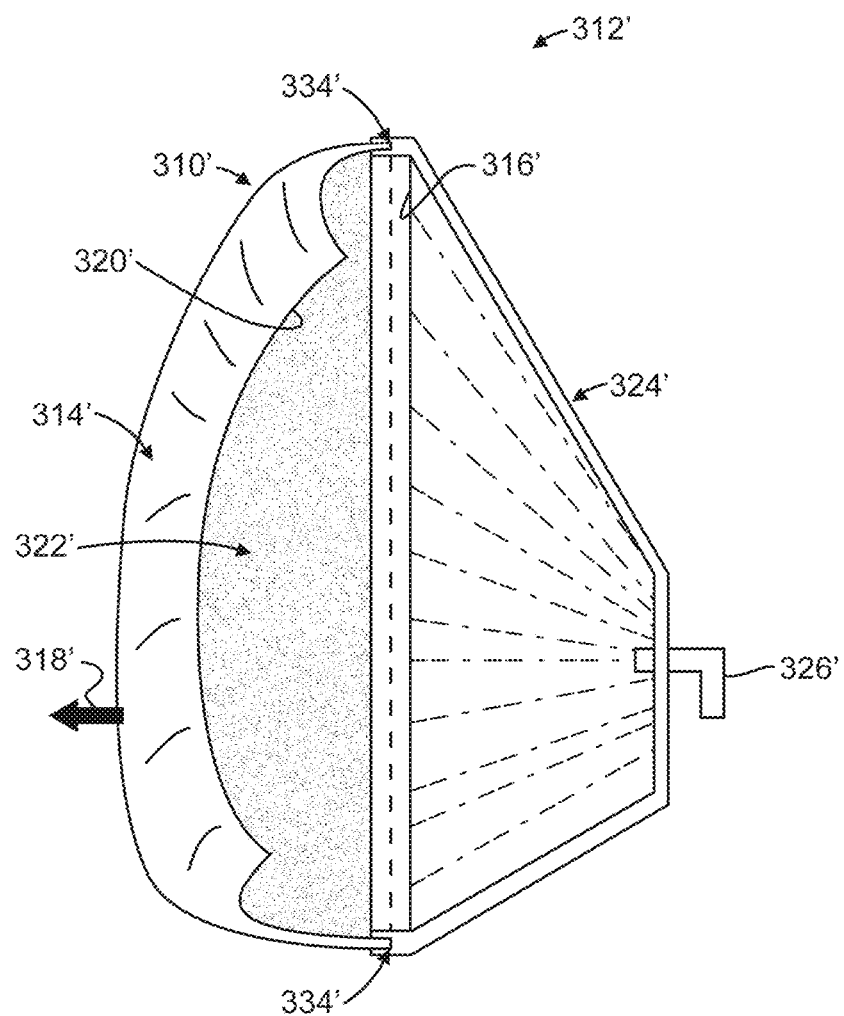
FIG. 9E is an elevational view of the respiratory mask of FIGS. 9A-D, partially cut away to reveal the J-shaped curl of the inner wall of the cushion and the outer wall of the cushion as it is joined to an outer periphery of the shell.
Figure 9F:
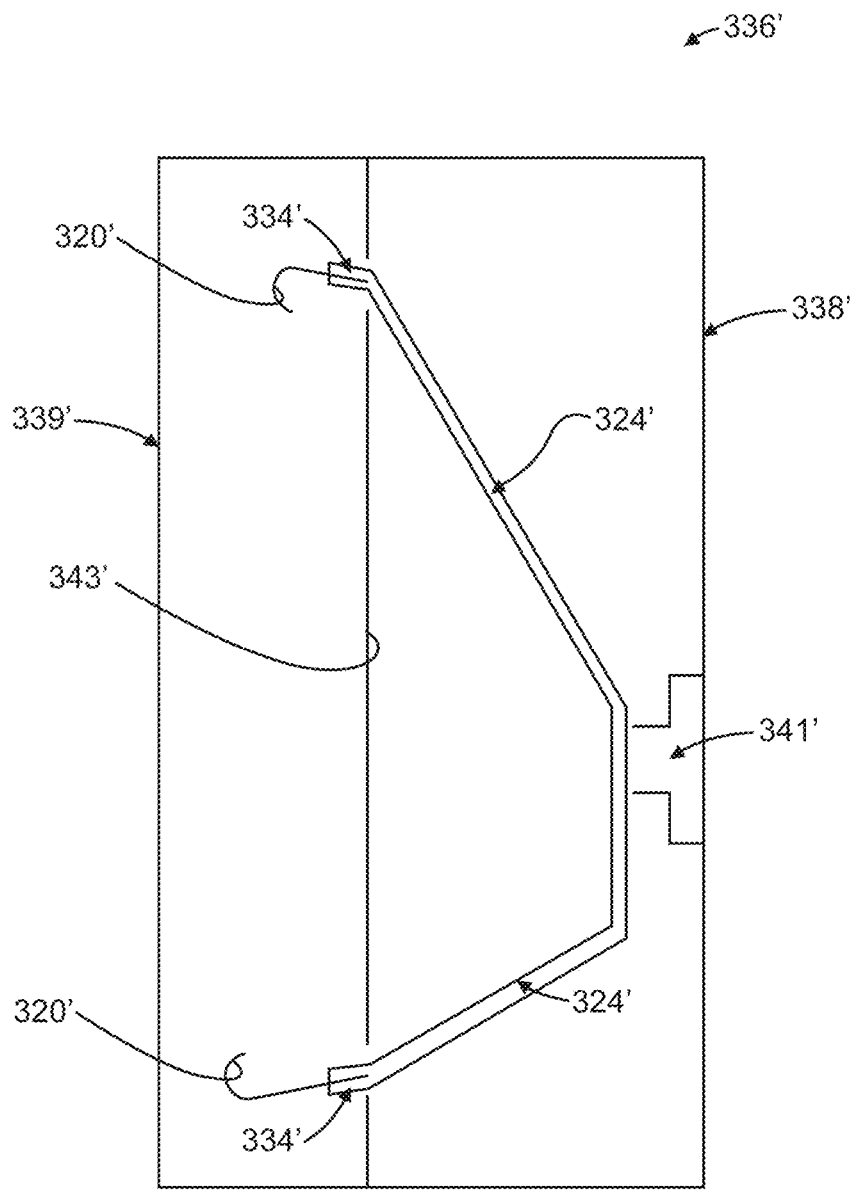
FIG. 9F is an apparatus of the present invention adapted to injection mold the shell of FIGS. 9A-E while joining the previously formed cushion to the shell.

With more specific reference to the product shown in FIGS. 9A-9E there is shown a unitary breathing mask cushion 310' for an interface 312' adapted for delivering oxygen to a patient in a hospital or emergency medical situation not necessarily related to obstructive sleep apnea. The embodiment of mask interface 312' shown is devised to cover both airways of the nose and mouth, as with the embodiment of FIG. 9. With continuing reference to FIGS. 9A-9E, interface 312' is disposable, being intended to be stored in sterile packaging (not shown) until used by a given patient then discarded when soiled in favor of another sterile interface, or simply discarded when no longer needed by the patient. For the sake of brevity hereinabove, numbered features of the hospital mask cushion 310' and interface 312' are referred to in the Drawings using primed designations since there are certain structures similar in some respects to those referenced by the same base numerals in the full face mask of FIG. 9. The principal difference between the unitary designs of FIGS. 9A-9E versus FIG. 9 is that FIG. 9 has a modular construction with several durable constituent parts that can be manually assembled together for use and disassembled for cleaning, repair or replacement of broken or worn-out parts, over a long-term period by a patient or caregiver. FIG. 9E illustrates more closely how the rigid plastic shell 324' is unitary with cushion 310' by means of the joint 334'. FIG. 9F depicts a mold assembly 336' having a first portion generally indicated at 338' and second portion 339'. A molten plastic is injected through port 341' into a space generally indicated at 324' of first portion 338' corresponding to shell 324'. The inboard curl 320' of cushion 310' (FIGS. 9A-9E) is entrapped with shell 324' at joint 334' (FIG. 9E). Cushion 310' is pre-formed by means of the various apparatus described elsewhere herein. Mold 336' has a parting line 343' that allows portions 338', 339' to be separated once the molding process is completed or prior to curing in further steps. Brackets 328', 328', 330' are provided on the outside of shell 324' to receive flexible straps extending around the patient's head, for securing interface 312'. The arrows 332' indicate lateral flexure of cushion 310' at the nose bridge of a wearer (not shown) in order to provide a tight comfortable yet soft sealing action.

Figure 8:
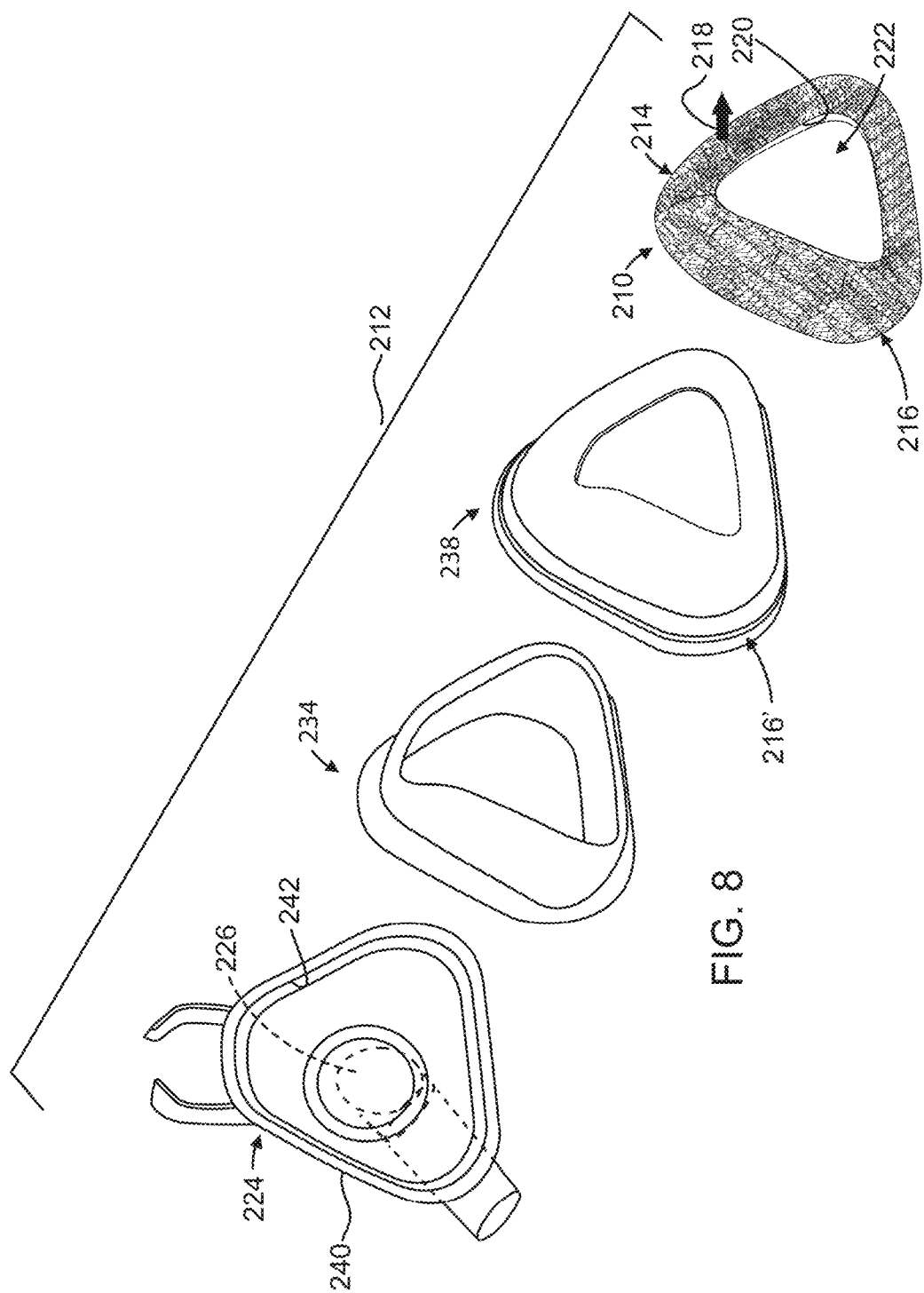
FIG. 8 is an exploded perspective view of yet another alternative interface for a breathing mask, having shell and preform surrounding the nose as in FIG. 7, a membranous flap assembly with rim snapped over the preform onto the shell and a cushion liner (without flange) situated atop the flap assembly, according to the present invention.
Figure 10A:
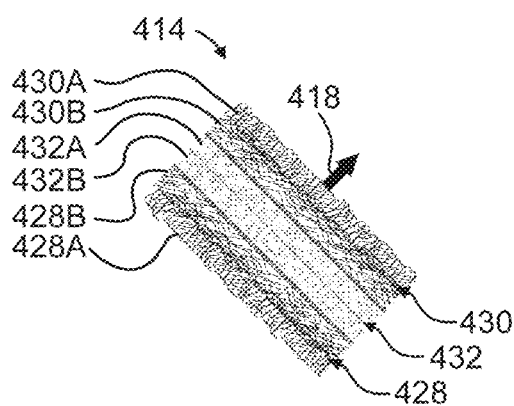
FIG. 10A is an enlarged view of the circular region delimited FIGS. 10A-10B in FIG. 10, showing a preferred laminar composite construction having dual layers of fleeced fabric wherein the loftier fleece side of each layer faces outwardly and the less lofty, smoother woven side faces inwardly, with a liquid impermeable barrier layer sandwiched between the juxtaposed woven sides, according to the present invention.
Figure 10B:
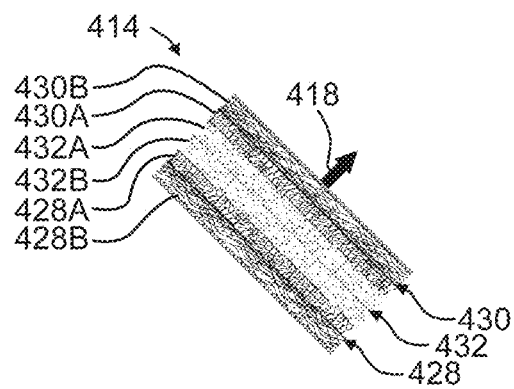
FIG. 10B is another enlarged view of the circular region delimited FIGS. 10A-10B in FIG. 10, showing an alternate preferred laminar composite construction having dual layers of fleeced fabric wherein the loftier fleece side of each layer faces inwardly and the less lofty/smoother woven side faces outwardly, with a liquid impermeable barrier layer sandwiched between the juxtaposed fleece sides, according to the present invention.
Figure 10:
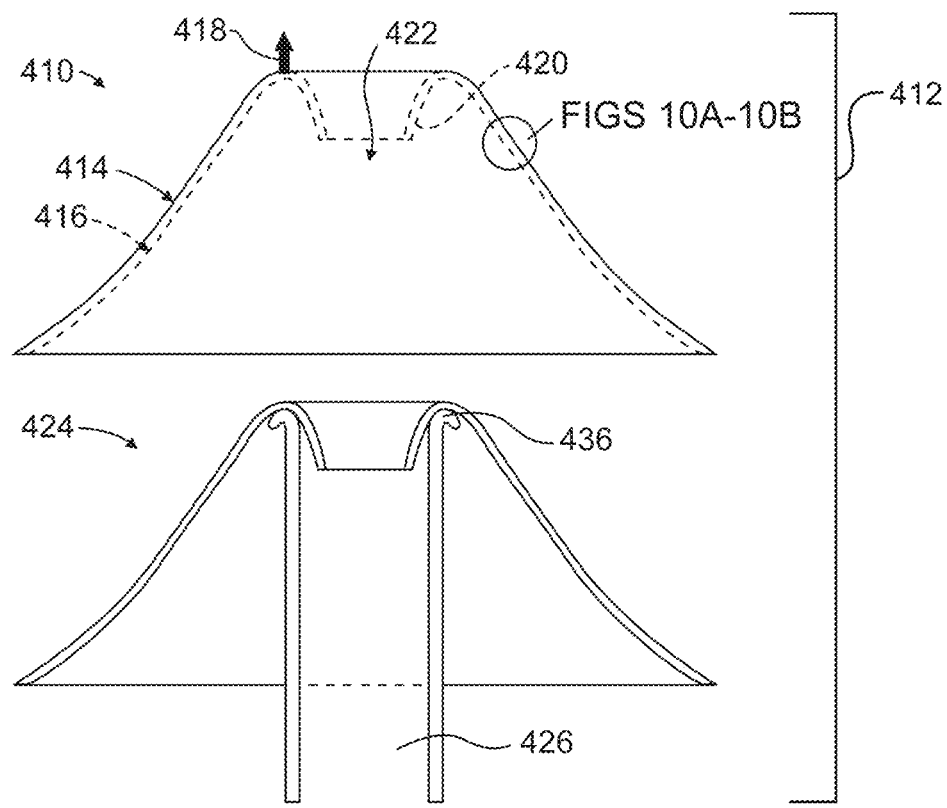
FIG. 10 is an exploded view showing a nose pillow assembly including a frustoconical base supported by a gas delivery tube and a nasal seal cushion constructed of a laminar fabric composite.

Alternately, in FIG. 10, the contour of cushion 410 has a three-dimensional frustoconical shape and is telescopically positioned over similarly shaped conventional nose pillow 424 having tubular inlet 426 adapted with a flattened terminal flare 436 axially supporting the pillow for stable alignment with the cushion such that J-shaped inboard curl 420 is securely captured within flare 436 as the cushion is positioned in contact with the pillow during use. Pillow 424 in this manner provides a mounting function for cushion 410, analogous to the telescoping relationship between cushion 110 and solid pre-form 134 (FIG. 7), as well as between similar solid pre-form 234 and membranous flapper 238 and cushion 210 resting in turn upon the flapper (FIG. 8).

Attention is now drawn to FIGS. 5A-5B and FIGS. 10A-10B, in conjunction with which the preferred construction of laminar composite body 14, 414 will be described. The embodiments of FIGS. 6-9 utilize the same or similar constructions as those discussed in greater detail as mentioned immediately above. Preferably, at least second layer 30, 430 is a fibrous material, more preferably a fleeced knit fabric having a puffy brushed surface 30A, 430A and a woven surface 30B, 430B, for example a sweatshirt fabric. Similarly, first layer 28, 428 may be a fleeced knit fabric such as a sweatshirt fabric having a puffy surface 28A, 428A and a woven surface 28B, 428B. It is further preferred that the second layer 30, 430, which is closest the patient, i.e., patient contacting portion 18, 118, 218, 318, 418 has puffy brushed surface 30A, 430A in direct contact with the patient's skin, which leaves woven surface 30B, 430B juxtaposed with sealant layer 32, 432. Alternatively, puffy surface 30B, 430B of second layer 30, 430 may be juxtaposed with sealant layer 32, 432. It is also preferred that first 28, 428 and second 30, 430 layers are each a fleeced fabric having a woven surface 28B, 428B and puffy brushed surface 30A, 430A with the woven surfaces of each layer being in direct contact with the elastomeric layer. Preferably, sealant layers 32A, 32B, 432A, 432B are applied onto each of the first 28, 428 and second 30, 430 layers, respectively, during the stretch-bonded lamination process herein. Accordingly, a transition zone 32C is indicated between sealant layers 32A and 32B in FIGS. 5A-5B to represent the sealant-to-sealant lamination of the coated layers 28, 30 and 428, 430 together according to the present process.

Preferably, cushion 10, 110, 210 is part of a generally open triangular shaped nosepiece of a Continuous Positive Air Pressure (CPAP) mask interface 12, 112, 212 conforming to the wearer's facial contours and intended to cover the nasal airway. More preferably, as shown in FIG. 9, cushion 310 covers airways of both the patient's nose and mouth in a so-called BiPAP mask interface 312. Referring to FIGS. 6-9, coupling portion 16, 116, 216, 316 of cushion 10, 110, 210, 310 is preferably flanged in order to adapt for sealing engagement with a complementary ridge 40, 140, 240, 340 and shelf 42, 142, 242, 342 of mask shell 24, 124, 224, 324, respectively. In FIG. 9, a ring 344 fits over cushion 310 and secures around a periphery 346 of shell 324 by means of a plurality of locking tangs 348.

Referring to FIGS. 11-40, some of the apparatus of the present invention is illustrated while devoid of substrate material being processed, in order to render more clarity to the structures thereof. Discussion of such apparatus will infer practice of the Applicant's method to the processed material (referred to numerically in parenthesis), as will be appreciated by those skilled in the art. However, in FIGS. 24A-24B and 25A-25C, there is explicitly shown the laminar material indicated at 14 in its various states of fabrication. FIG. 9F has already been described in conjunction with the shell 324' and cushion 310' formed by mold 336'.

Figure 11:
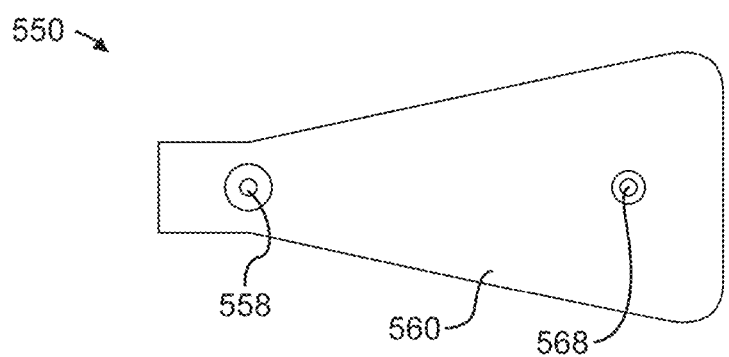
FIG. 11 is an elevational view of an applicator for distributing the liquid impermeable barrier layer onto fabric of the laminar composite of the present invention.
Figure 12:
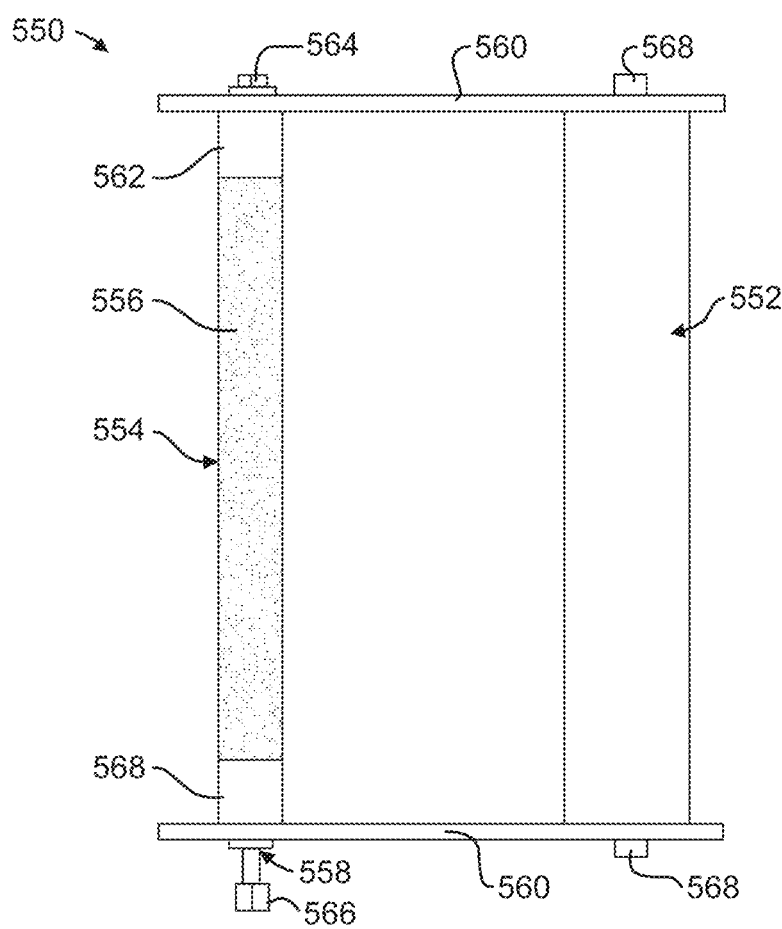
FIG. 12 is a top view of the applicator of FIG. 11, showing an assembly having a handle and a roller with porous surface for spreading the liquid impermeable barrier material supplied to the roller, according to the present invention.

More particularly, FIGS. 11-12 generally show an applicator assembly 550 for depositing the sealant material layer (32, 432) that imparts the vapor impermeable barrier properties to fabric of the preferred laminar composite body (14, 114, 214, 314) of the present invention. Applicator 550 is an assembly having a handle generally indicated at 552 and a roller generally indicated at 554 with porous surface 556 for spreading a preferred liquid impermeable sealant material (not shown) supplied to the roller via a tubular inlet and bushing sub-assembly generally indicated at 558, to which is attached via nut 566 to a 90-degree swivel fitting and hose leading to the material supply (not shown). Roller 554 and handle 552 extend between a pair of opposed brackets 560, 560, the roller being plugged at one end 562 and secured to one of the brackets by fastener 564 while tubular inlet and bushing sub-assembly 558 secures the opposed end 568 of the roller to the other of the brackets. The pair of fasteners 568, 568 secures handle 552 to the pair of brackets 560, 560, respectively, as shown in FIG. 12. Overall length of roller 554 may be about 7 inches, in view of the end uses for the finished article as contemplated herein.

Figure 13:
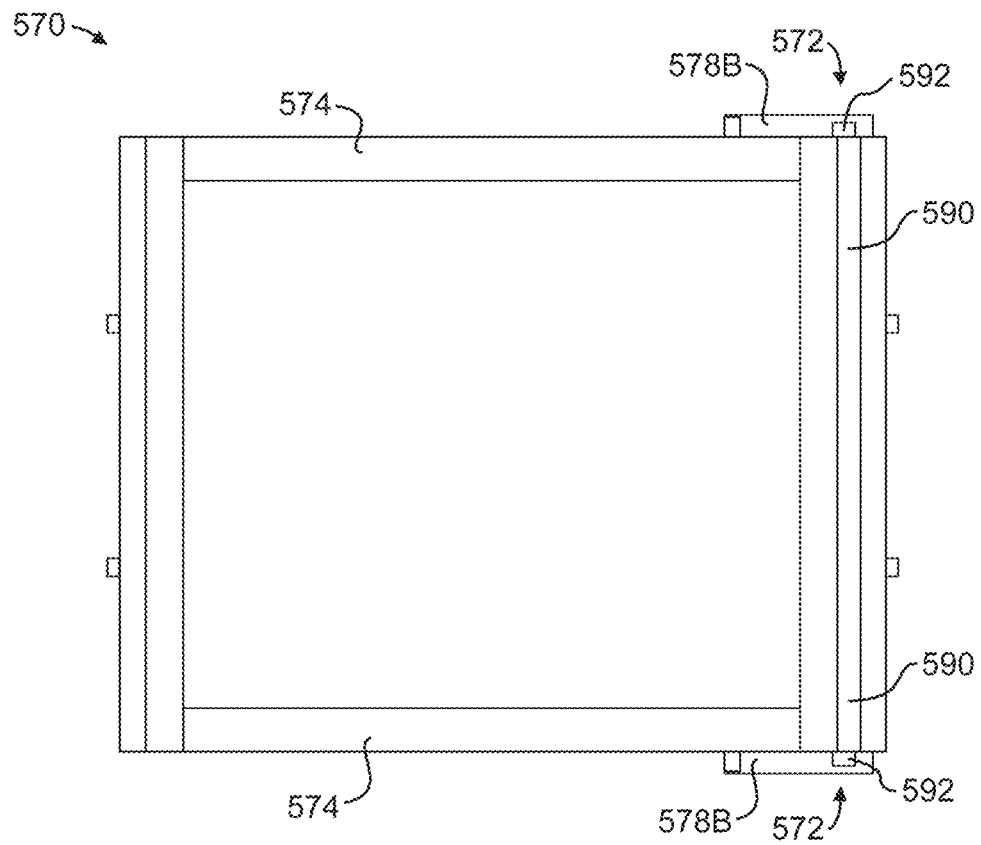
FIG. 13 is a top view of a the application fixture that operates with the applicator of FIGS. 11-12, according to the present invention.
Figure 14A:
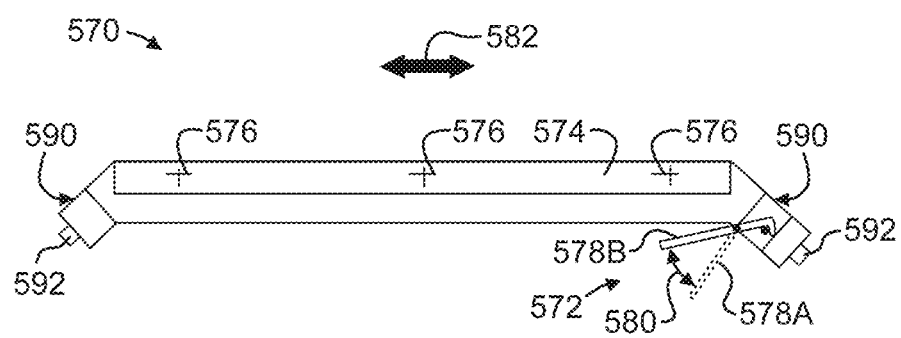
FIG. 14A is an elevational view of the side of fixture of FIG. 13 showing a hinged clamp for holding one or more of the fabric layers in a selectively stretched condition for the applicator to distribute the liquid impermeable barrier material onto the fabric, according to the present invention.
Figure 14B:
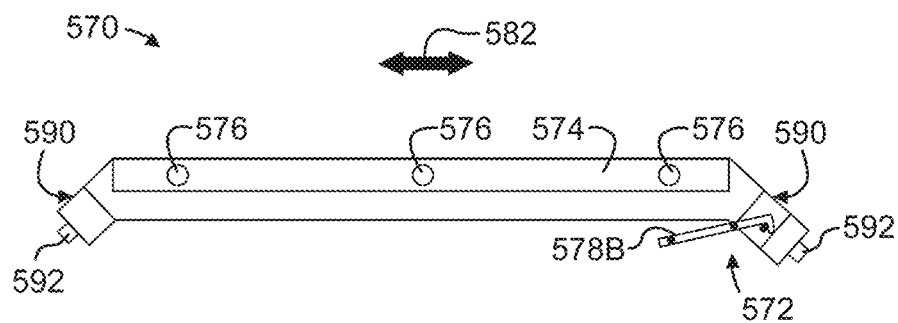
FIG. 14B is an elevational view of the opposite side of the fixture of FIG. 13 showing a similar hinged clamp for holding one or more of the fabric layers in a selectively stretched cross direction for the applicator to distribute the liquid impermeable barrier material onto the fabric, according to the present invention.
Figure 15:
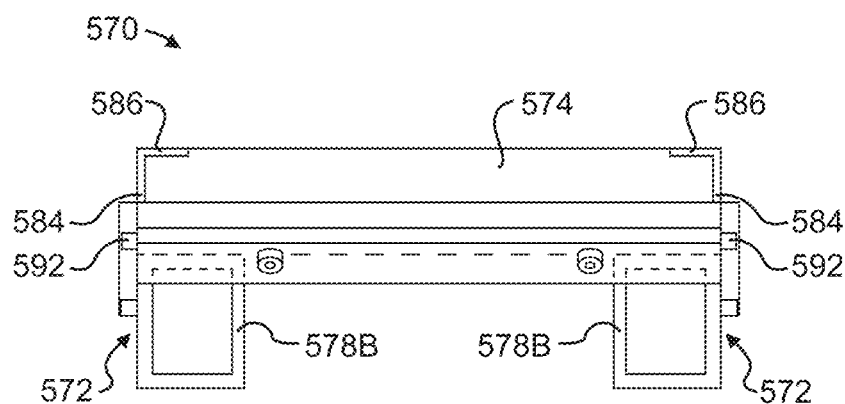
FIG. 15 is an elevational view of an end of the fixture of FIG. 14, showing height adjustment bars for accommodating different thicknesses of fabric layer, including a ledge and clamp for gripping the fabric layer and stretching it in a orthogonal (machine) direction, according to the present invention.

Referring to FIG. 13, there is generally shown an application fixture 570, intended to operate with applicator 550 of FIGS. 11-12. Fixture 570 holds a fabric layer (28, 30, 428, 430) in tension sufficiently to avoid any buckling therein to keep the layer smooth while the applicator, particularly roller 554, is depositing a sealant material layer (32, 432) thereon. In FIG. 14A there is further depicted a hinged clamp, generally indicated at 572 movable between lever positions indicated at 578A and 578B (Arrow 580) for holding one or more of the fabric layers (28, 30, 428, 430) in a selectively stretched condition in a longitudinal direction (Arrow 582) for applicator 550 to dispense and distribute sealant material for the liquid impermeable barrier layer (32, 432) onto the stretched fabric, according to the present invention. A pair of laterally opposed L-shaped plates 574, 574 each have an adjustable height that may be raised and lowered by means of counter-sunk slotted holes 576, 576, 576 according to the thickness of the fibrous layer (28, 30, 428, 430) and/or the sealant layer (32, 432) entrapped by the plates, in which case shims (not shown) can be used to further maintain the height adjustment. In operation, clamp screws 576, 576, 576 are loosened and the desired height is set for the fabric (28, 30, 428, 430) and sealant layer (32, 432) thickness by loosening the three set screws. Using calibrated bars the height is set by sliding the bar under flange 586 and tightening screws 576. The fabric (28, 30, 428, 430) is laid in the fixture jig and clamp jaws generally indicated at 590, 590 are opened. As fabric (28, 30, 428, 430) is set in clamp 590, 590, the clamp screws 592 are tightened. With clamp 590 in "up" position the fabric is placed in the clamp and the clamp screws are tightened. The hinge spring adjustment 578A-578B is set for proper percentage stretch of fabric (28, 30, 428, 430). Applicator 550 is then used, as the application process is begun by triggering the flow of sealant (32, 432) with the applicator set on the adjustment bars 574, 574. It has been found acceptable for about two passes of applicator 550 to be made, with any excess wiped off then clamp screws 576 are loosened to allow the fabric (28, 30, 428, 430) to relax and the curing process to proceed. Referring to FIG. 14B a similar hinged clamp 572 is provided for holding one or more of the fabric layers (28, 30, 428, 430) in a selectively stretched cross direction (Arrow 584) for applicator 550 to dispense and distribute the liquid impermeable barrier material (32, 432) onto the fabric. Referring to FIG. 15 showing height adjustment bars 584 are used for accommodating different thicknesses of fabric layer (28, 30, 428, 430), including a recessed ledge 586 and clamp 572 for gripping the fabric layer and stretching it in a direction orthogonal to Arrow 582, according to the present invention.

Figure 16:
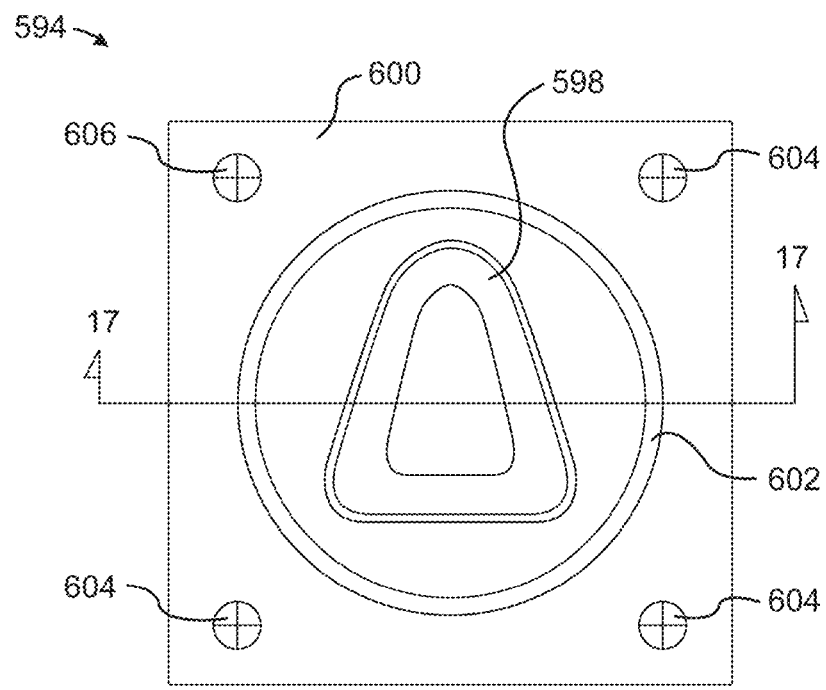
FIG. 16 is a top view of a cavity portion of a molding fixture (FIG. 24), according to the present invention.
Figure 17:
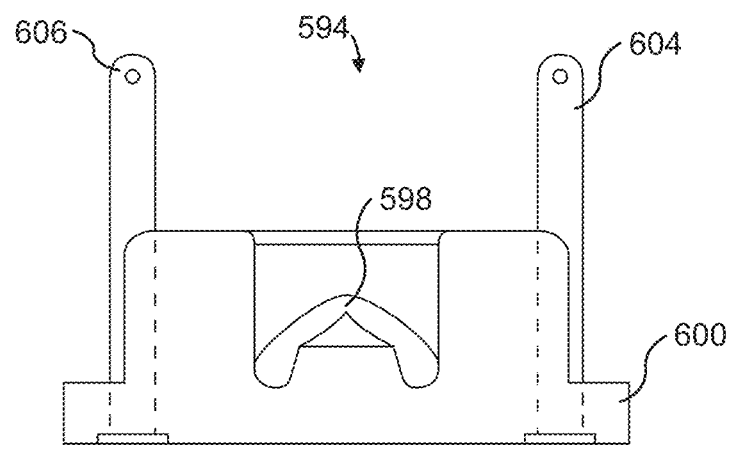
FIG. 17 is a sectional view, taken along the Lines 17-17 of FIG. 16.
Figure 16A:
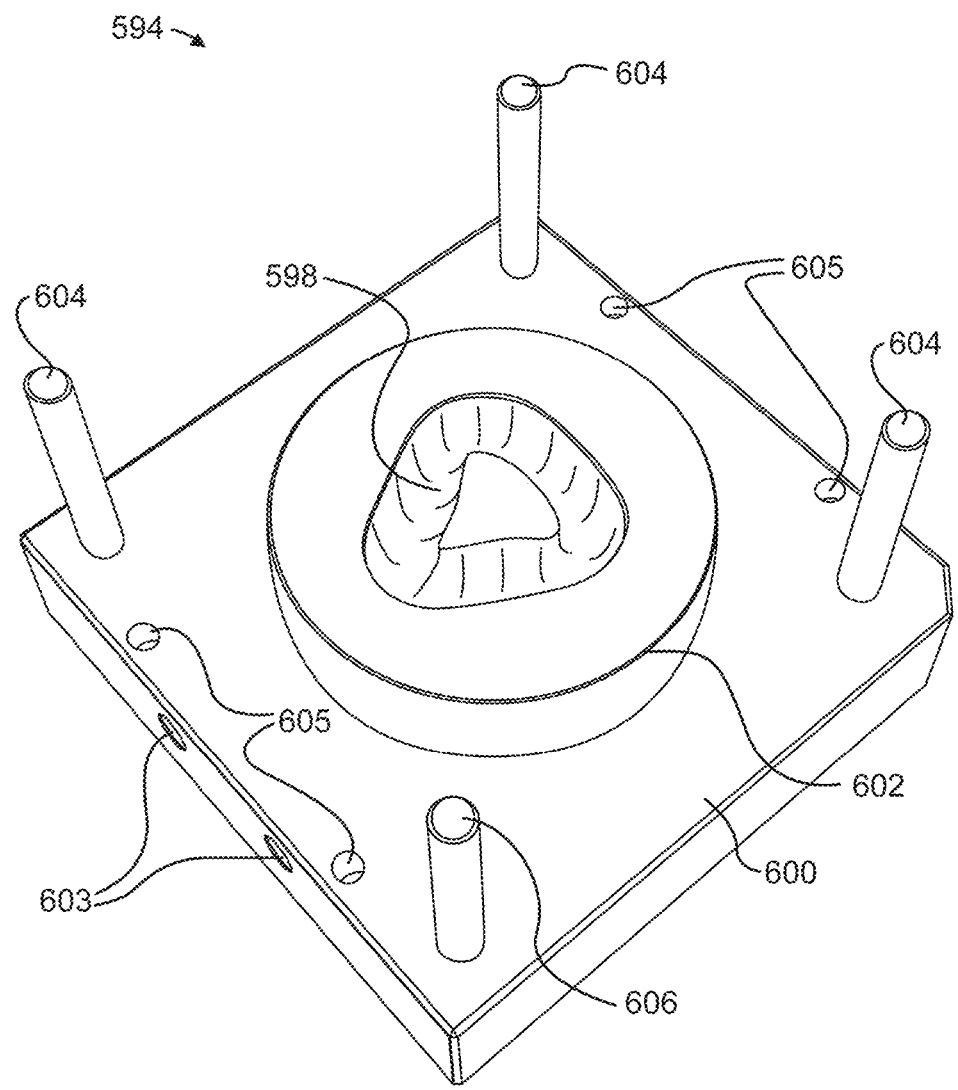
FIG. 16A is a perspective view of the mold cavity of FIGS. 16-17, showing its anvil-shaped protrusion from the cavity recess in a raised circular platform of the mold platen.

Referring to FIGS. 16, 16A and 17, there is generally shown a cavity portion 594 of a molding assembly later generally depicted at 596 together with its other various features in FIG. 24 and FIGS. 24A-24B, in FIG. 25 and in FIGS. 25A-C and FIG. 26. Cavity portion 594 has a female depression 598 formed in the mold platen 600 corresponding to the three-dimensional contours of the cushion (10, 110) along with a surrounding rim 602. There are three guide pins 604 and an offset guide pin 606 for alignment with other structures of mold assembly 596 referred to above in this Paragraph.

Figure 18:
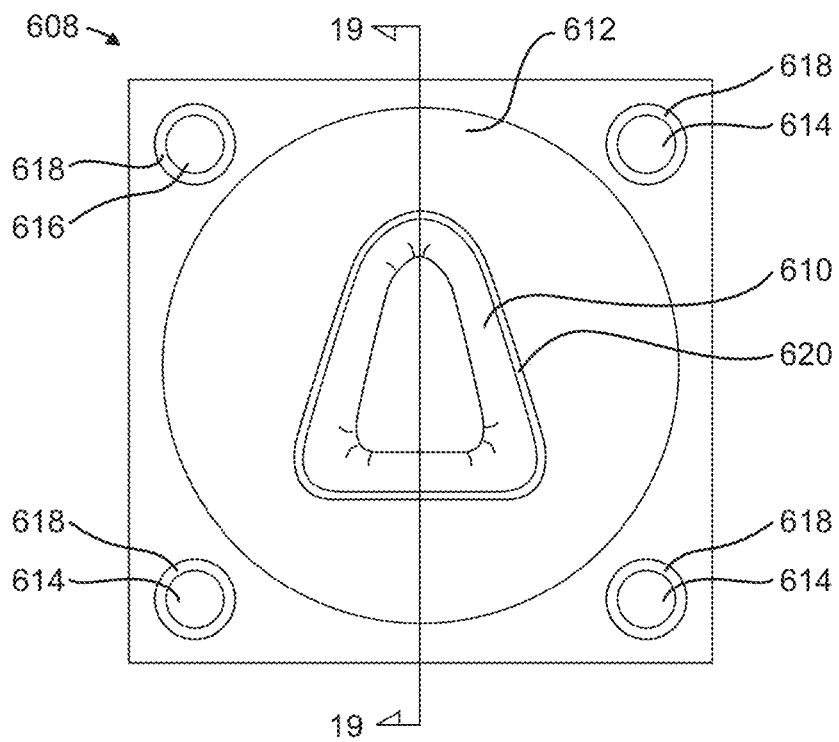
FIG. 18 is a top view of a plug portion of the molding fixture operable with the cavity of FIGS. 16-17, according to the present invention.
Figure 18A:
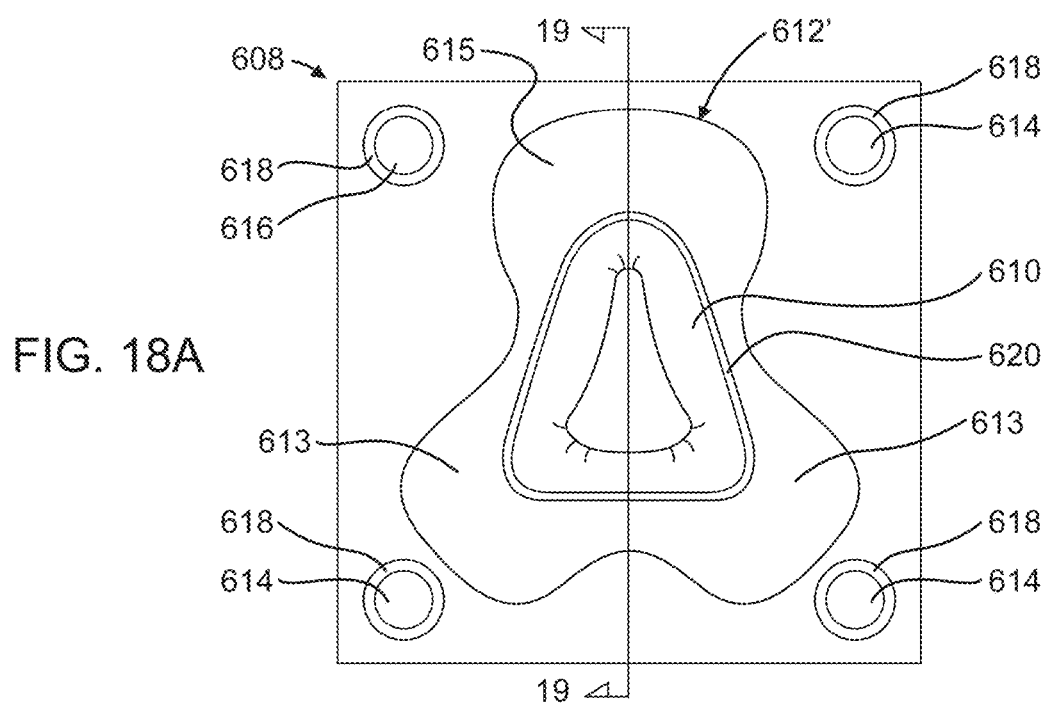
FIG. 18A is a top view of an alternate clover-leaf shaped platform of the plug portion of FIG. 18 and of FIG. 19 below, the lobed configuration advantageously distributing the lines of force exerted upon the cushion fabric as the plug and cavity are moved together to close the mold assembly.
Figure 19:
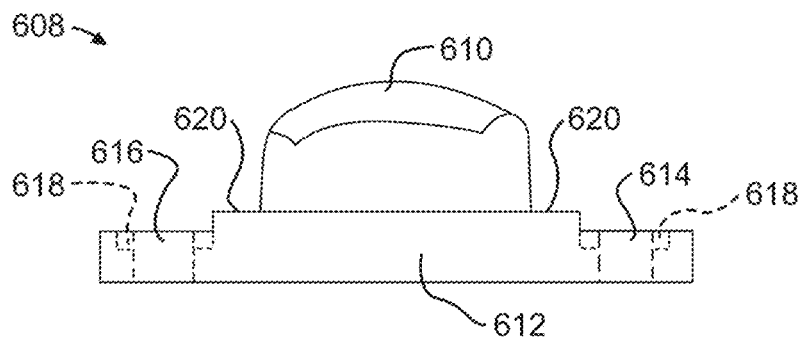
FIG. 19 is a sectional view taken along the Lines 19-19 of FIG. 18 and FIG. 18A, respectively.

Referring to FIGS. 18, 18A and 19, there is generally shown a plug portion 608 of molding fixture 596 operable with cavity portion 594 of FIGS. 16-17. Plug portion 608 has a male forming member 610 projecting from a platen 612 having formed therein three apertures 614, 614, 614 for receiving the guide pins 604, 604, 604 from cavity portion 594. An offset guide pin aperture 616 receives guide pin 606 from cavity portion 594. A recess 618, 618, 618, 618 is provided in each guide aperture 614, 614, 614, 616 for fabric slide and a secondary draft 620 is formed surrounding male member 610. Draft 620 cooperates with a circular ridge 632 described in FIGS. 20-21 to securely hold the laminar blank in mold 594. In FIG. 18A platen 612' has an alternative lobed profile, generally indicated at 612', including a pair of corner lobes 613, 613 and an apical lobe 615 corresponding to the section where the nasal bridge of the cushion (10) is formed.

Figure 20:
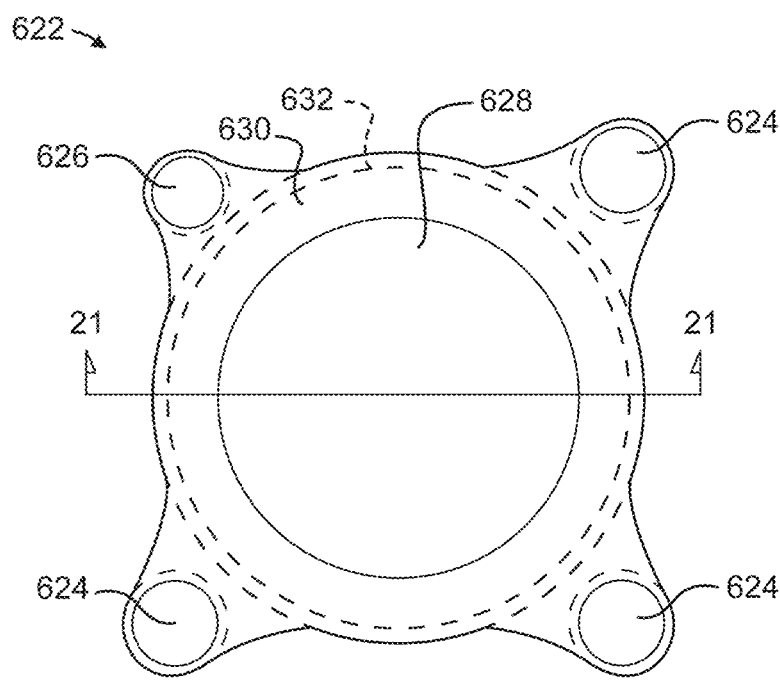
FIG. 20 is a top view of a circular fabric holder and retainer, situated between the cavity (FIGS. 16-17) and plug (FIGS. 18-19) of the molding fixture (FIG. 24), according to the invention.
Figure 20A:
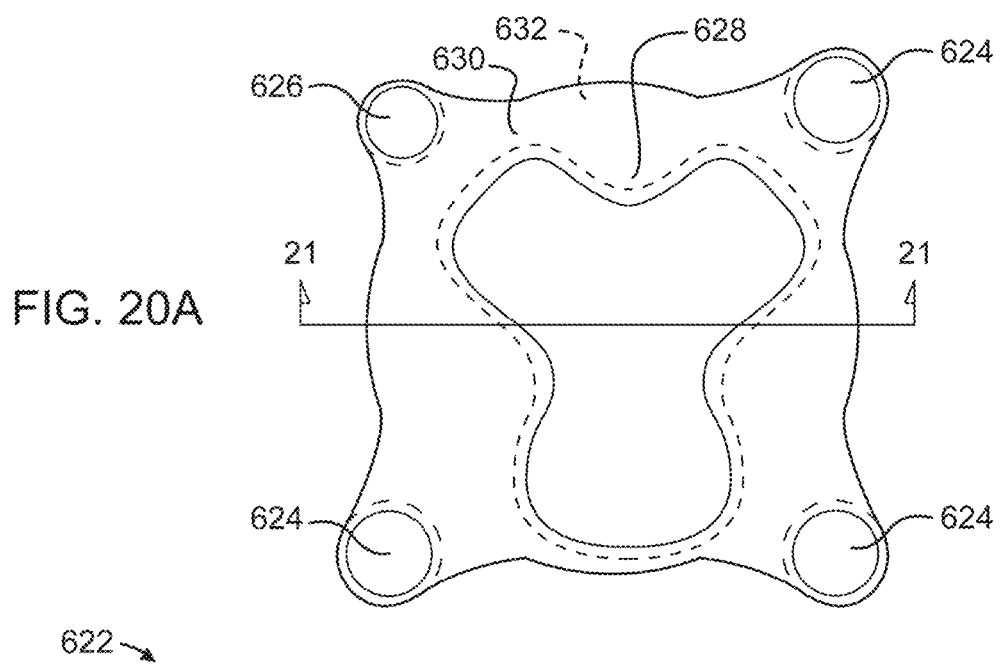
FIG. 20A is a top view of an alternate clover-leaf shaped retainer which articulates with the cloverleaf-shaped platform of the plug, such that the cushion fabric is captured between the retainer and platform, advantageously distributing the lines of force exerted upon the fabric as the mold is closed, according to the invention.
Figure 21:
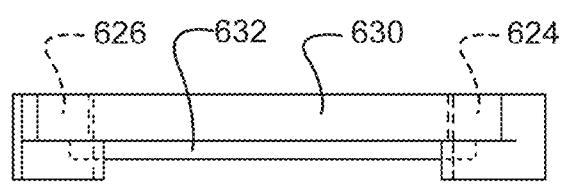
FIG. 21 is a sectional view, taken along the Lines 21-21 of FIG. 20 and FIG. 20A, respectively, according to the invention.

Referring to FIGS. 20, 20A and 21, there is generally shown a fabric holder and retainer, i.e., a tambour 622, situated between cavity portion 594 (FIGS. 16, 16A and 17) and plug portion 608 (FIGS. 18, 18A and 19) of molding fixture 596 (FIGS. 24, 24A-B and 25A-C). Three guide holes 624, 624, 624 receive guide pins 604, 604, 604 and an offset guide hole 626 receives offset guide pin 606, respectively. There is a central opening 628 formed in a platen 630 and circular ridge 632 that cooperates with draft 620 to hold the laminar blank tightly between the ridge and the draft when mold assembly 594 is closed. The lobular profile of tambour 622 shown in FIG. 20A corresponds to that of FIG. 18A, such that the lines of force are applied to the laminar material that is entrapped between the articulating outer periphery of platen 612' and inner periphery 628 of tambour 622 when the lobes are juxtaposed, as discussed above in conjunction with FIG. 20A.

Figure 22:
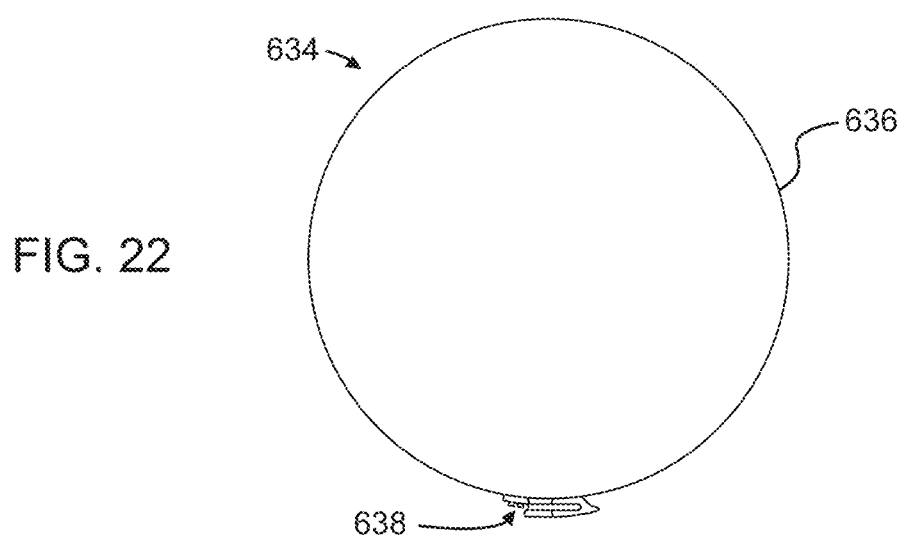
FIG. 22 is a top view of a tambour that may be used for retaining the fabric composite in a radially stretched condition between the portions of the molding fixture (FIG. 24), according to the invention.
Figure 23:
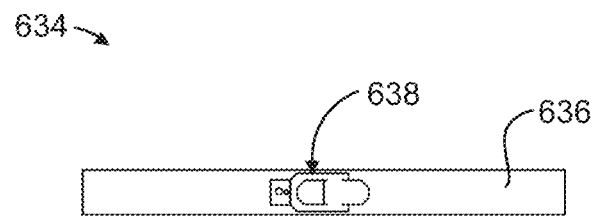
FIG. 23 an elevational view further showing the strapping clamp of the tambour in FIG. 22.
Figure 24:
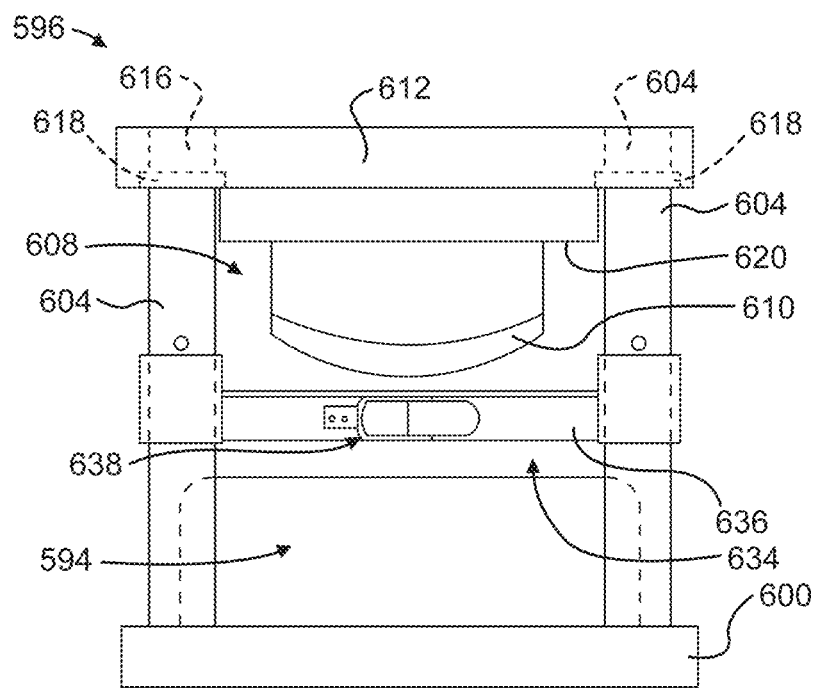
FIG. 24 is an elevational view of the molding fixture shown in an open position with the assembly of its constituent elements depicted in FIGS. 16-23, according to the present invention.
Figure 24A:
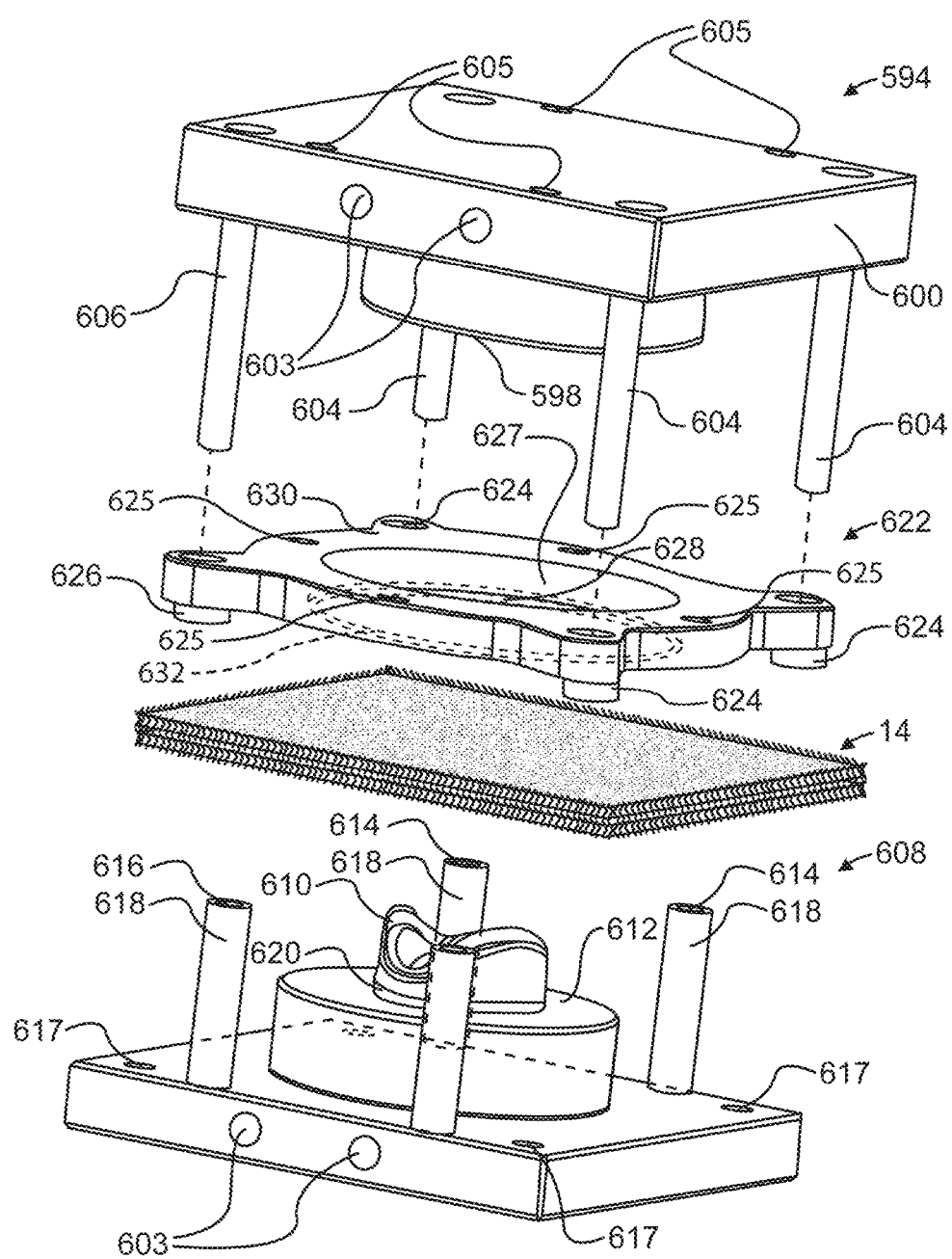
FIG. 24A is an exploded perspective view of the mold assembly of FIG. 24, showing the fabric positioned between the plug and retainer components, respectively, with the mold open.
Figure 24B:
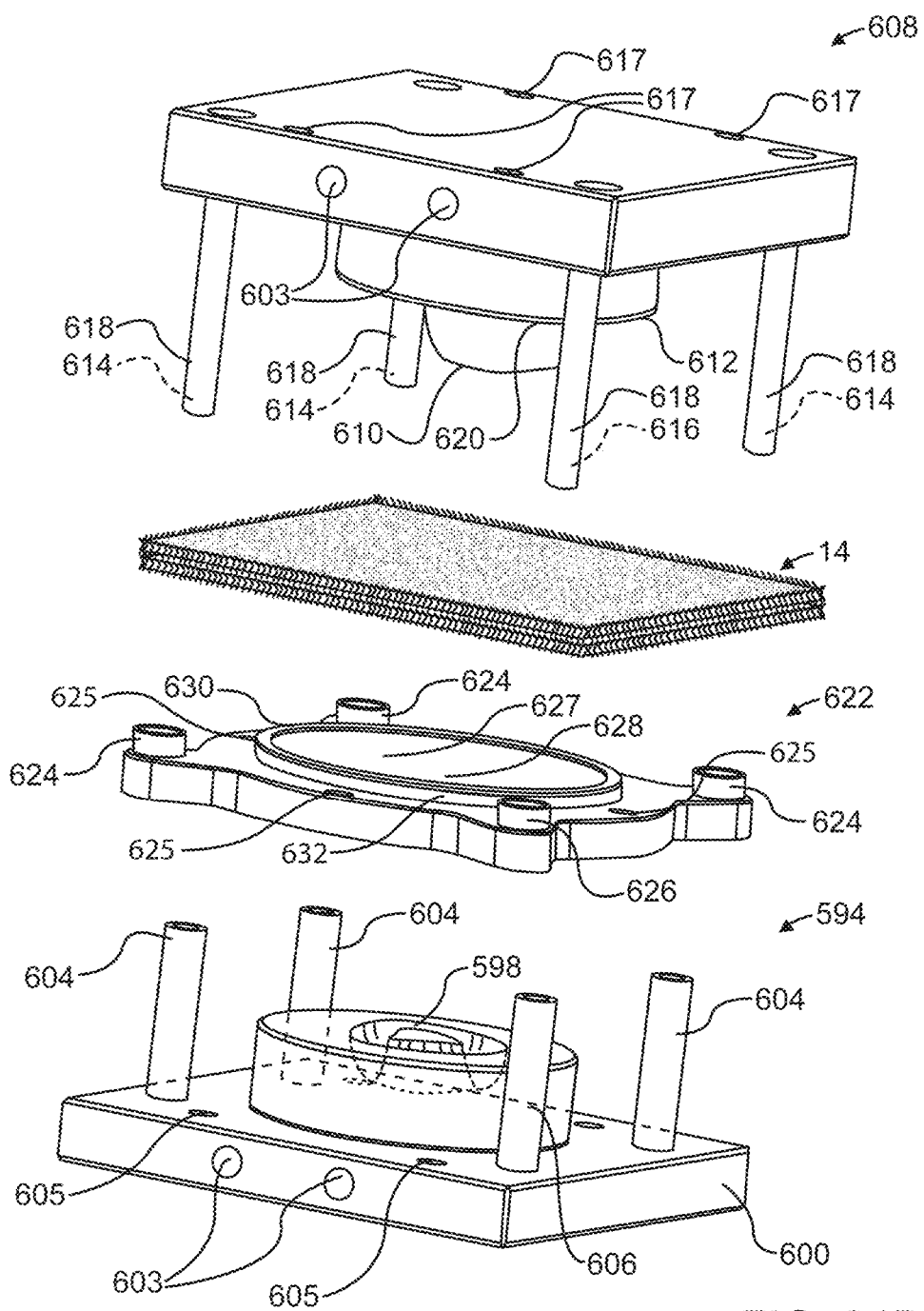
FIG. 24B is an exploded perspective view showing the cavity and plug components inverted from the view of FIG. 24A, revealing the anvil-shaped protrusion in the cavity that forms the form-fitting, self-adjusting nose bridge portion in the cushion fabric as the mold assembly is closed (FIGS. 25A-25B), according to the invention.
Figure 25:
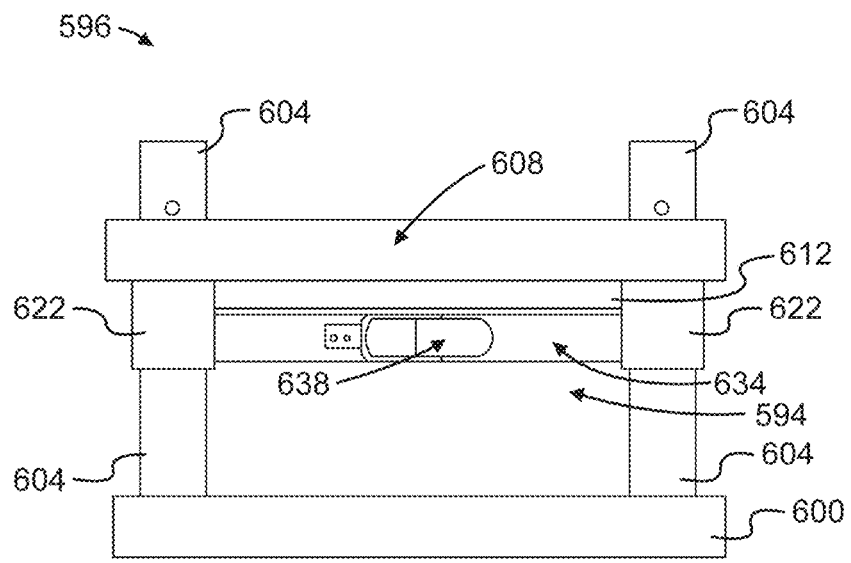
FIG. 25 is an elevational view of the molding fixture of FIG. 24, shown in its closed position, according to the present invention.
Figure 26:
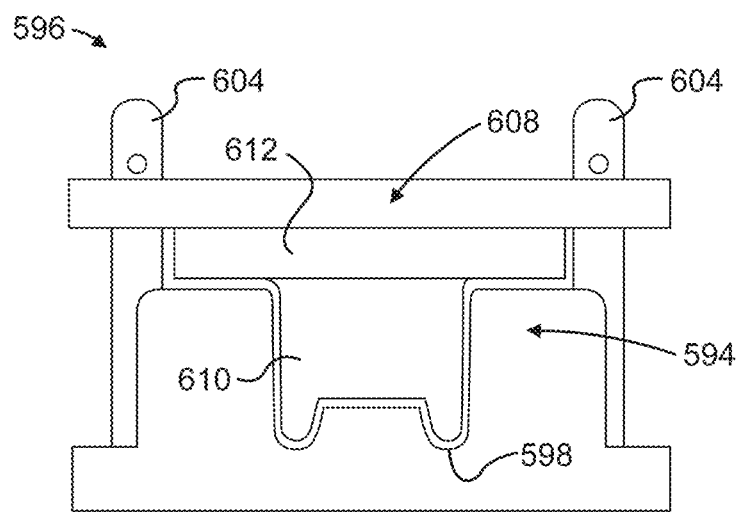
FIG. 26 is another elevational view of the molding assembly of FIG. 25, partially cut-away.

Referring to FIGS. 22-23 there is generally shown an optional strap 634 for secondarily retaining the laminar fabric composite layers (28, 30, 428, 430) within tambour 622, in a radially stretched condition between the portions of the molding fixture 596 (FIG. 24, 24A-B). Referring to FIG. 23, tambour 634 has a rim 636 and strapping clamp 638 to immobilize the fabric.

Figure 25A:
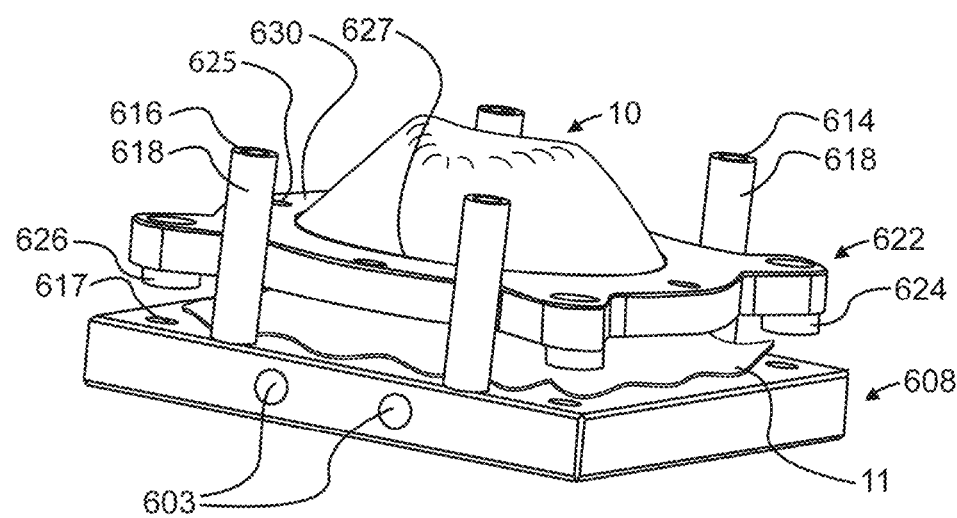
FIG. 25A is an exploded perspective view of the retainer and plug components of the mold assembly of FIGS. 25-26, sequentially closed with the cushion fabric entrapped, prior to the cavity component being assembled therewith (FIG. 25B)
Figure 25B:
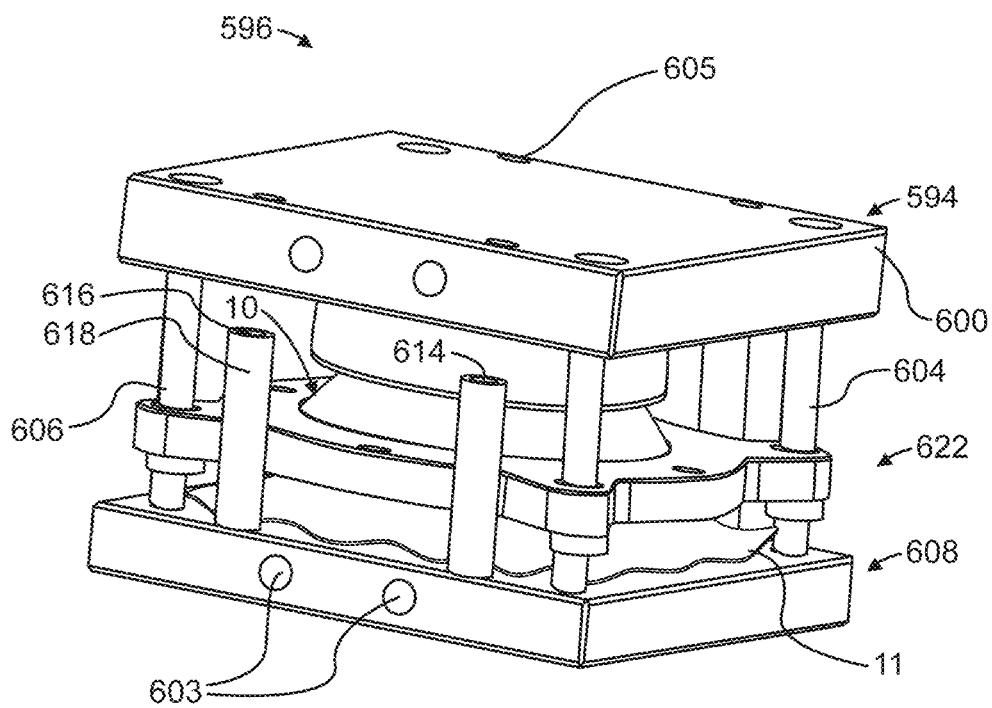
FIG. 25B is an exploded perspective sequential view of the complete mold assembly components, prior to the fastening of the pins between mold components, according to the invention.
Figure 25C:
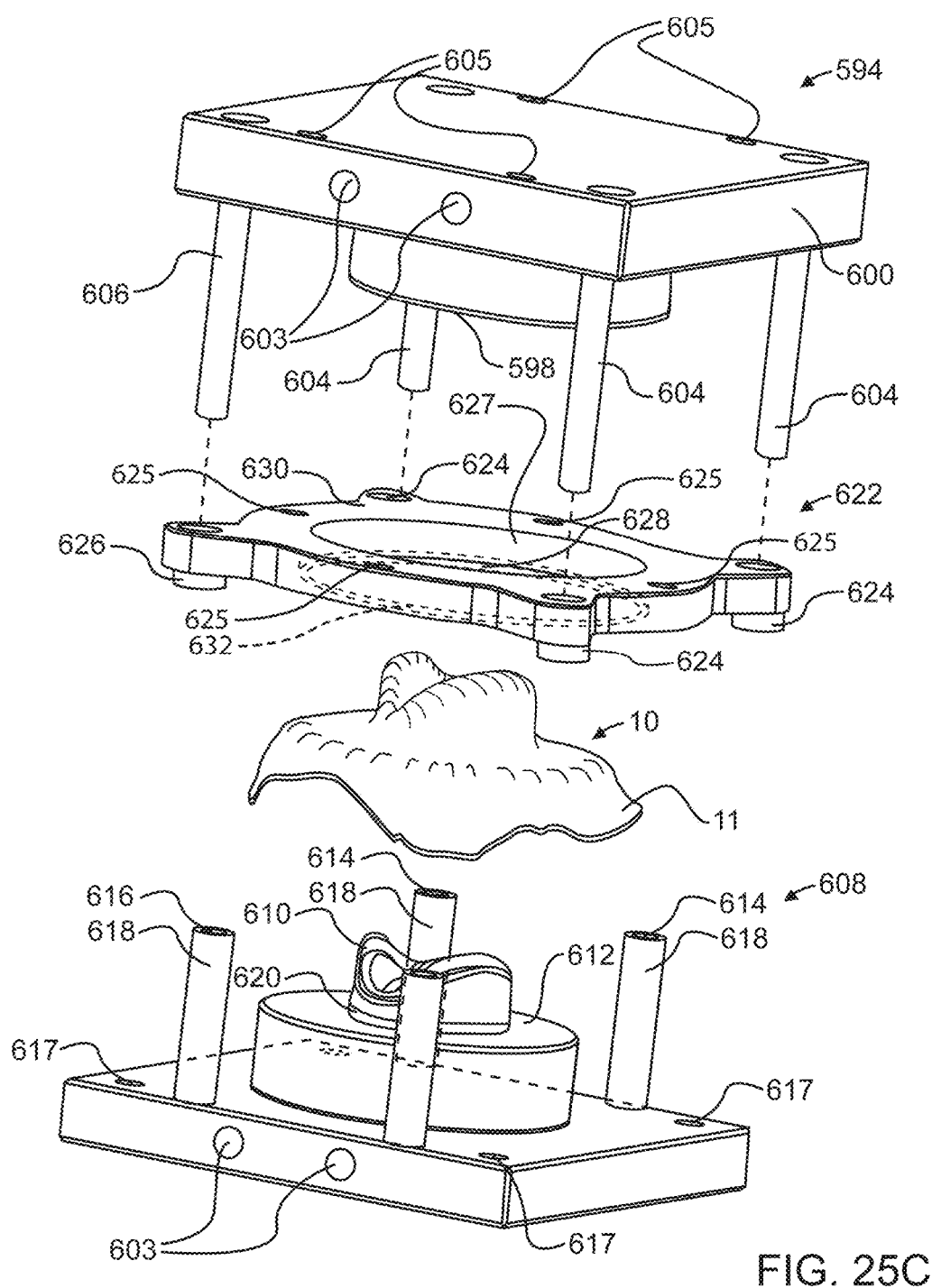
FIG. 25C is an exploded perspective sequential view of the complete mold assembly components open following the molding cycle, showing the cushion blank ejected from the mold, prior to the further processing by the trim fixtures (FIGS. 27-40)

Referring to FIGS. 24 and 24A-B, molding fixture 596 is generally shown in an open position with its assembly of components having been enumerated hereinabove relative to FIGS. 16-23. FIGS. 24A and 24B are inversions of one another so that the structure and relationship between cavity 594, tambour 622, laminar material 14 and plug 608 may be more fully appreciated by those skilled in the art. Molding fixture 596 is generally shown in its closed position in FIGS. 25, 25A-C and 26. In FIGS. 24A-B and 25A-C there is shown a pair of ports 603 for heating and cooling the cavity 594 and plug 608 according to the process herein. In FIGS. 25A-C, the tambour is moved against the plug 608 such that the inner periphery surface 627 of the tambour opening 628 and surface of ridge 598 of the plug are juxtaposed with one another with the material 14 being formed thereby into a blank pre-form of cushion 10 with excess material 11 to be trimmed from the blank by the fixtures discussed in FIGS. 27-40 below.

Referring again to FIGS. 24-25 inclusive, to close the cavity 594 and plug 608 and tambour 622, the following members must be aligned and drawn together with the fabric 14 between the plug and the tambour, as will now be described. Pins 604, 604, 604 and locator pin 606 pass from the cavity portion 594 through apertures 624, 624, 624 and offset locator aperture 626, thence into apertures 617 in plug 608 so that the cavity and tambour and plug can only be assembled in one orientation. Pins 614, 614, 614 from plug 608 pass alongside tambour 622 and are received in similar apertures 605, 605, 605 and offset pin 616 is received in the remaining fourth aperture 605 that is offset from the rest.

Figure 27:
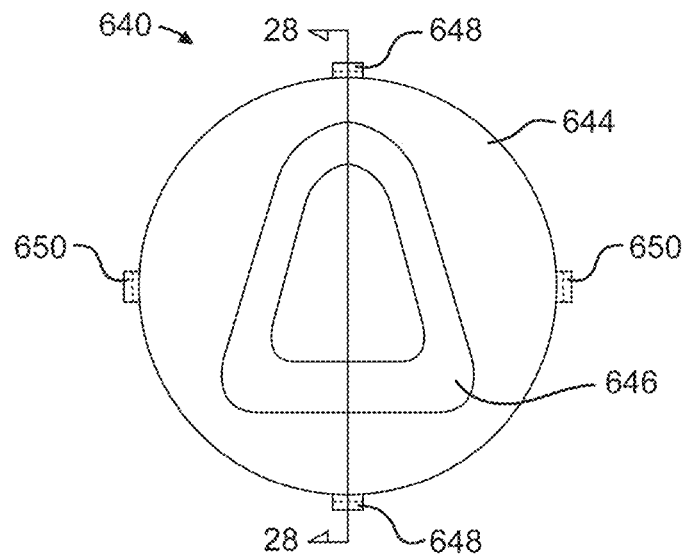
FIG. 27 is a top view of a plug for an inner trim fixture, according to the present invention.
Figure 28:
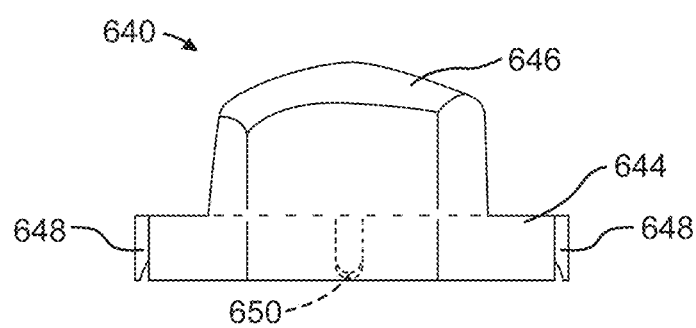
FIG. 28 is a sectional view taken along lines 28-28 of FIG. 27.
Figure 29:
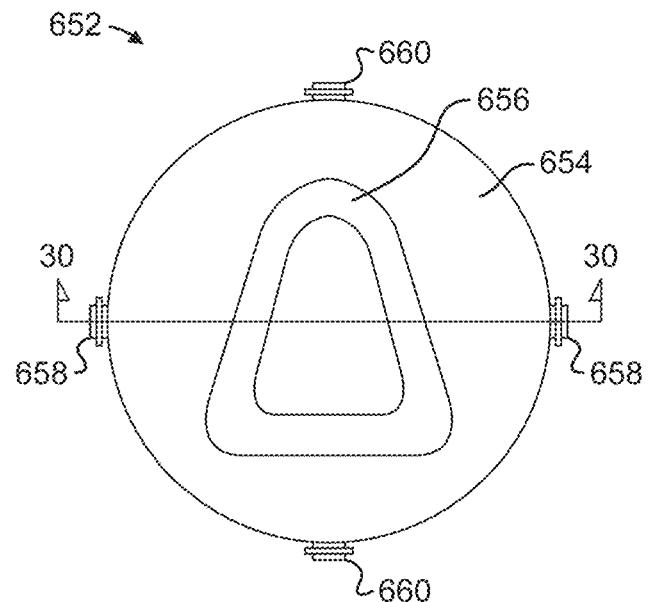
FIG. 29 is a top view of a cavity for the inner trim fixture, operable with the plug of FIGS. 27-28, according to the present invention.
Figure 30:
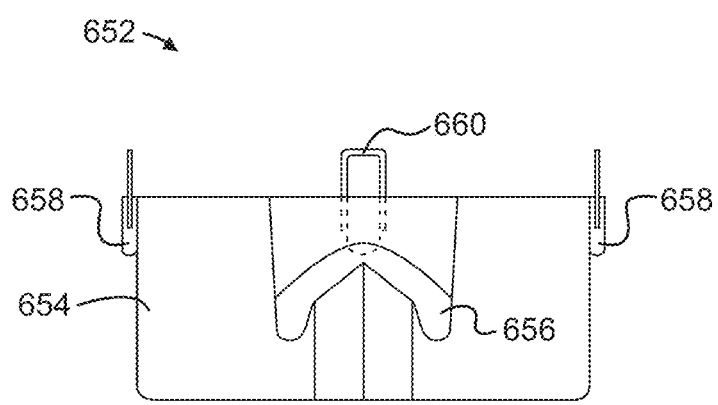
FIG. 30 is a sectional view taken along the lines 30-30 of FIG. 29.
Figure 36:
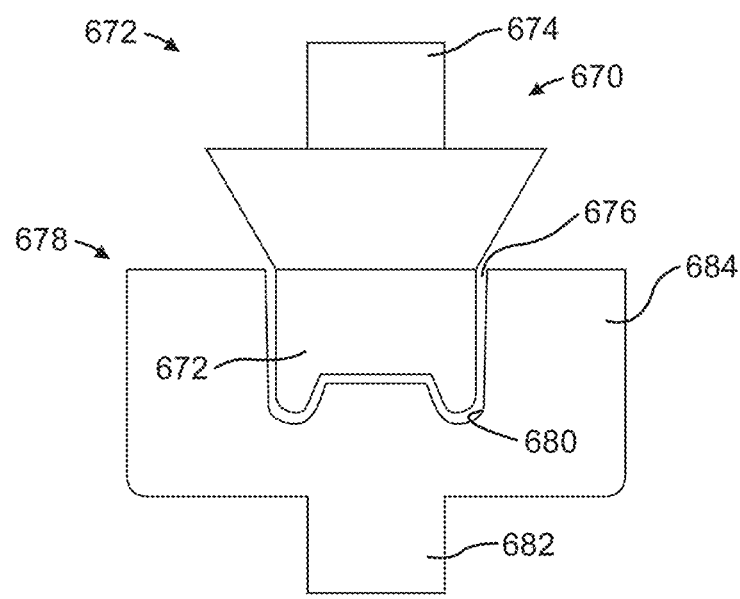
FIG. 36 is a sectional view taken along lines 36-36 of FIG. 35.
Figure 37:
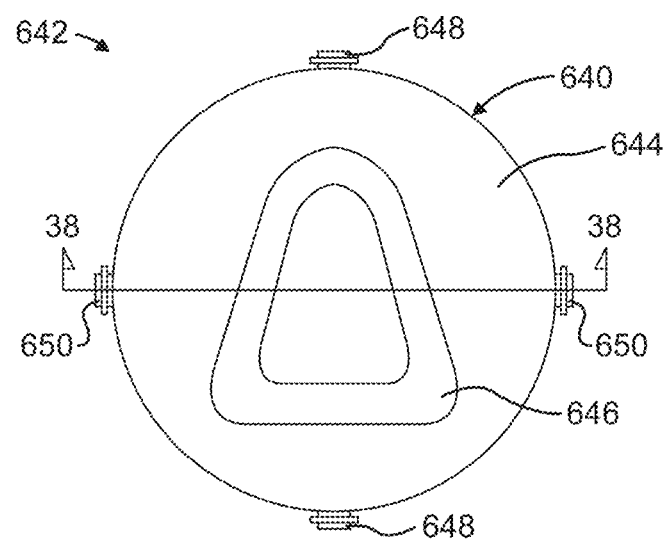
FIG. 37 is a top view of the inner trim fixture assembled with plug (FIGS. 27-28) and cavity (FIGS. 29-30)
Figure 38:
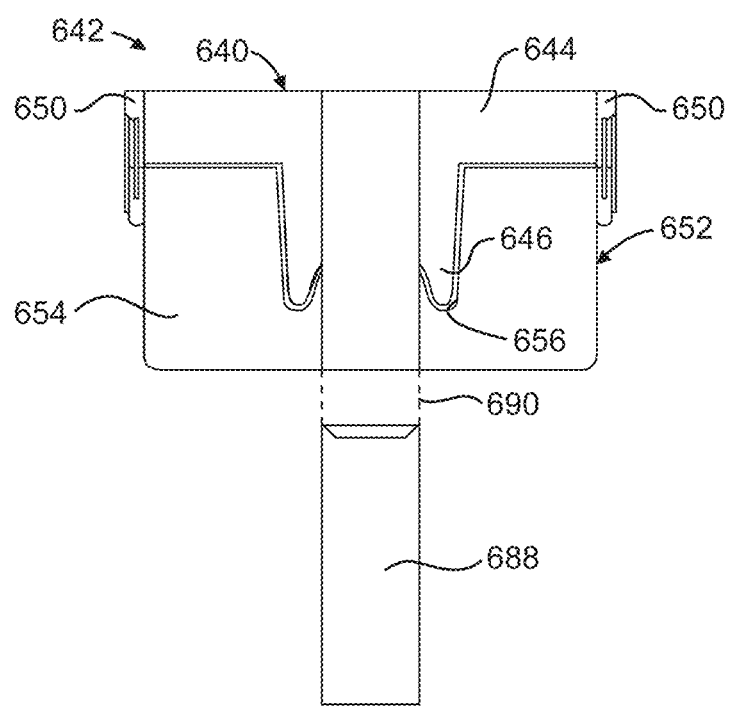
FIG. 38 is a sectional view taken along lines 38-38 of FIG. 37, further showing a preferred cutter tool.
Figure 39:
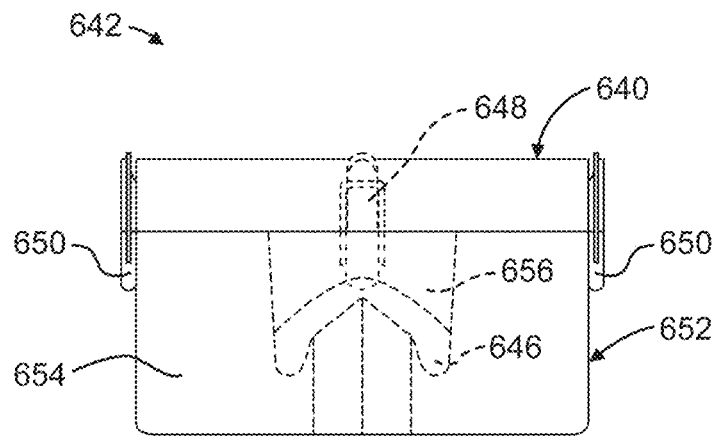
FIG. 39 is an elevational view of the inner trim fixture assembly, with enumerated structures indicated partly by the hidden (dashed) lines.
Figure 40:
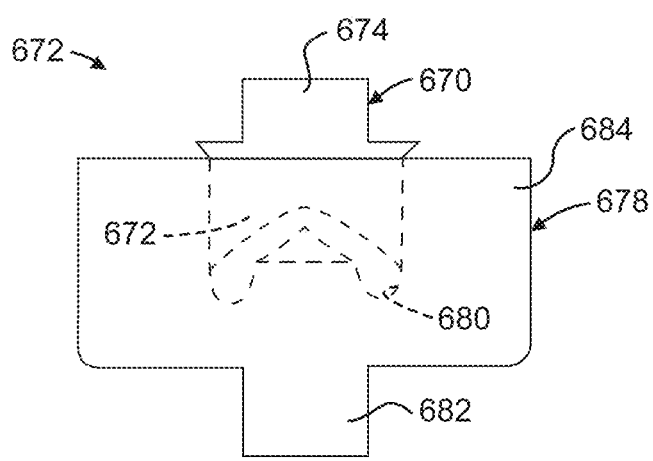
FIG. 40 is an elevational view of the outer trim fixture assembly, with internal structures indicated by the hidden (dashed) lines.

Referring to FIGS. 27-28 there is depicted a plug portion 640 for an inner trim fixture assembly generally shown at 642 in FIGS. 37-39. Plug 640 has a circular platen 644 with pairs of alignment members 648, 648 and 650, 650 and raised forming member 656. Referring to FIGS. 29-30 there is generally shown a cavity portion 652 operable with plug 640 of inner trim fixture 642, including platen 654, with alignment members 658, 658 and 660, 660. In FIG. 39 is shown a closed position of inner trim assembly 642 including structures enumerated in FIG. 38. Referring to FIG. 40, outer trim fixture assembly 672 is shown in closed position, with structures enumerated in FIGS. 35-36 indicated where appropriate by hidden (dashed) lines.

Figure 31:
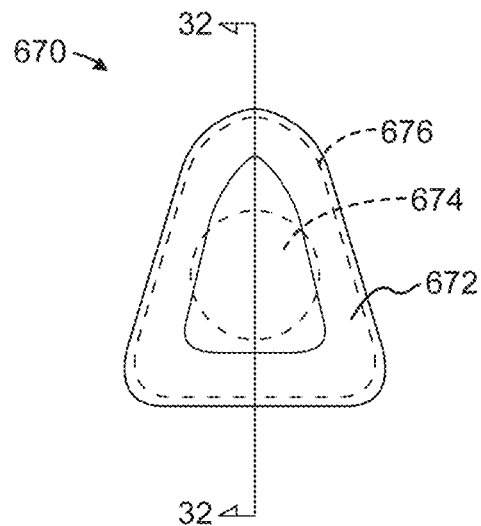
FIG. 31 is a top view of a plug for an outer trim fixture, according to the present invention.
Figure 32:
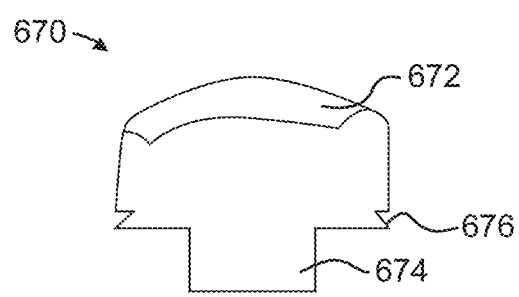
FIG. 32 is a sectional view taken along the lines 32-32 of FIG. 31.
Figure 33:
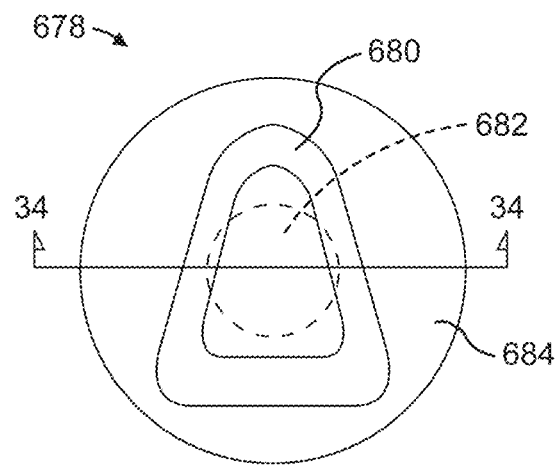
FIG. 33 is a top view of a cavity for the outer trim fixture, operable with the plug of FIGS. 31-32, according to the present invention.
Figure 34:
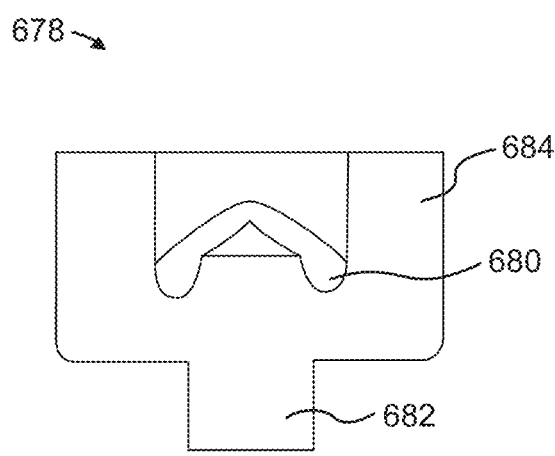
FIG. 34 is a sectional view taken along lines 34-34 of FIG. 33.
Figure 35:
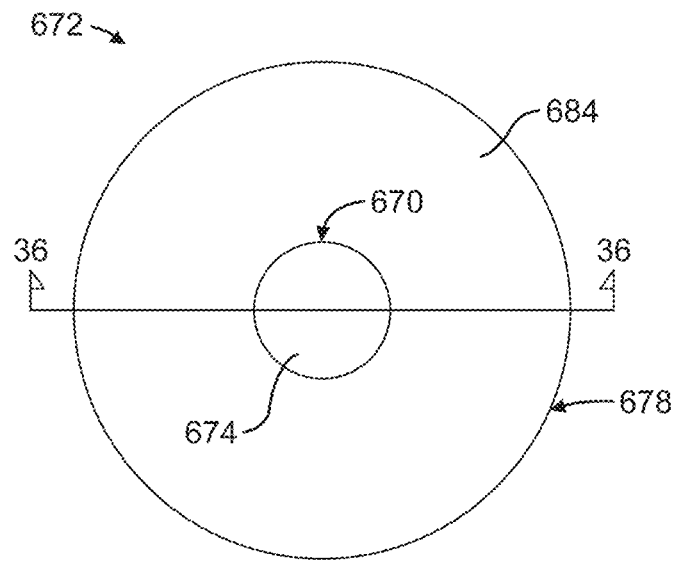
FIG. 35 is a top view of the outer trim fixture assembled with plug (FIGS. 31-32) and cavity (FIGS. 33-34)

Referring to FIGS. 31-32 there is depicted a plug portion 670 for an outer trim fixture assembly generally shown at 672 in FIGS. 35-36 and 40, the plug having male forming member 672 with base 674 and undercut relief 676 (dotted lines). Referring to FIGS. 33-34, a cavity portion is generally shown at 678 having depression 680, base 682 (dotted lines) and platen 684. Cavity 678 is operable with plug 670 of outer trim fixture 672, articulating as illustrated in the assembled outer trim fixture 672 of FIGS. 35-36 and 40, and further having an opening 686 through which passes a preferred cutter tool 688 along dotted lines 690, the outer trim assembly shown in closed position by FIG. 40.

Figure 41:
FIG. 41 is a photograph of the Model V-5 Stiffness Tester instrument, manufactured and operated by Taber Industries of Tonawanda, N.Y., showing one of the test swatches taken from the laminar composite laid out in FIG. 42, made according to the present invention, and from which data of Table 1 was generated.
Figure 42:
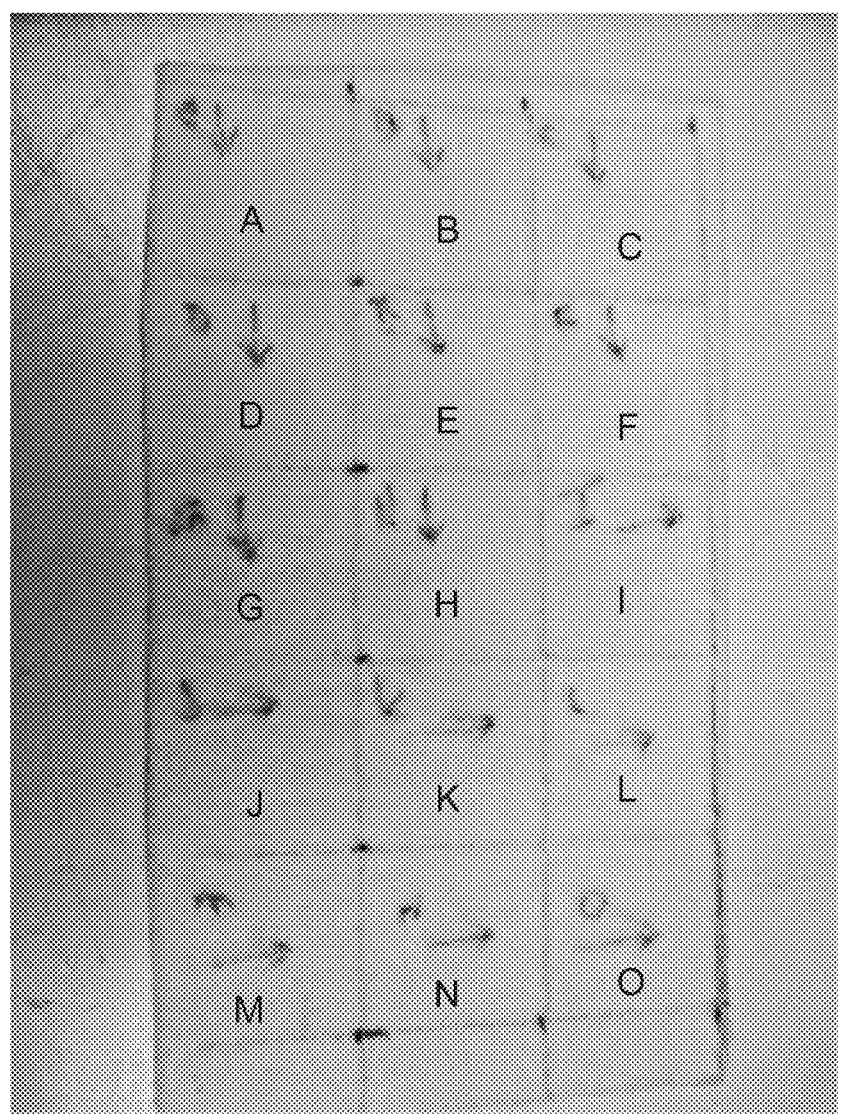
FIG. 42 is a photograph taken of a laminar composite of the present invention showing the sample material swatches laid out for testing by the instrument of FIG. 41.

Referring to FIG. 41 there is shown photographed the Model V-5 Stiffness Tester instrument, manufactured and operated by Taber Industries of Tonawanda, N.Y., having one of the test swatches taken from the laminar composite sample sheet laid out in FIG. 42. The Table 1 data was generated from use of the FIG. 41 instrument on the sample of FIG. 41. From this data, it is clear that Taber Stiffness measurements ranged from about 4 to about 10 Taber Stiffness Units, according to the particular swatches hand-marked A-O and with printed markings for easier identification.

According to the present invention there is generally provided a method of making a breathing mask cushion (10, 110, 210, and 310 in FIGS. 1-9). Reference numerals for particular product features described in the method are noted parenthetically below. The embodiment of a nose pillow cushion (410 in FIG. 10) could also be constructed using the same general method of the invention, yet differing in accord with the resultant frustoconical shape. The method generally includes the steps of providing a mold, generally shown at 596 having plug 608 with male shaping member 610 and female cavity 594, as previously discussed. First (28) and second (30) fibrous layers are provided, along with a third, fluid barrier layer (32) between the first and second fibrous layers. The layers (28, 30, 32) are superposed with one another between cavity 594 and shaping member 610 as mold 596 is closed. Mold 596 is heated, curing the elastomer (32) and bonding the fibrous layers (28, 30) together into a laminar composite body (14, 114, 214, 314, 414) preferably exhibiting a Taber Stiffness Value between about 4 to about 10 Taber Stiffness Units. Mold 596 is opened and a blank (not shown) removed. Preferably, a fabric having a knit surface (30B) and an opposite puffy brushed surface (30A) is provided as the second fibrous layer (28). More preferably, the elastomer (32A) is applied to knit surface (30B) of second layer (30). Also preferably, a knit surface (30B) and an opposite puffy brushed surface (30A) are provided as the first layer (28). More preferably, the elastomer (32A) is applied to the knit side of each of the first (28) and second (30) fibrous layers. Alternatively, the elastomer (32A) is applied to the puffy brushed side (30A) of each of the first (28) and second (30) fibrous layers. Still preferably, a flowable, self-leveling silicone elastomer (32A, 32A) is applied to either of the first (28) and second (30) layers. More preferably, the flowable, self-leveling silicone elastomer is applied to either of the first (28) and second (30)

layers. Again more preferably, a spreadable silicone elastomer paste is applied to one or both of the first (28) and second (30) layers.

According to a preferred embodiment of the present invention there is provided a method of making a cushion for a Continuous Positive Air Pressure or Bi-level Positive Airway Pressure (BiPAP) mask. The method includes the steps of providing a mold 596 having a male shaping member 610 and a female cavity 594, providing a first fibrous layer (28) and a second fibrous layer (30) superposed on the first layer, each layer presenting a knit surface (30B) and a puffy brushed surface (30A), applying a silicone elastomer (32) to a surface of at least one fibrous layer, interposing the layers between the shaping member and cavity and closing the mold. Mold 596 is heated, curing elastomer (32) and bonding fibrous layers (30A, 30B) together into a laminar composite body (14, 114, 214, 314, 414) exhibiting a Taber Stiffness value between about 4 to about 10 Taber Stiffness Units. The mold is opened and the finished cushion is removed. Preferably, a flowable, self-leveling silicone elastomer is applied; alternatively, a spreadable silicone elastomer paste is applied, according to the description provided herein.

Example 1

Silicone on Smooth Side

A commonly available sweat shirt material (SSM) is used having one-sided fleece, which can be made of cotton, synthetic or a cotton-synthetic blend of fibers. In this case, 85% polyester/15% cotton fleece SSM was used. A layer of silicone elastomer as described below in this Example 1 is applied to a thickness of 0.010-0.030 inches on the smooth, non-fleeced side of the SSM. The combined thickness of the SSM and elastomer is about 0.125 inches. The above was cured using a hair dryer. The above SSM on its own stretches multi-directionally without separating from cloth substrate or elastomeric layer. Another layer of same or similar silicone compound is applied to a second layer of SSM or other cloth in a similar manner. Then the laminar composite is held in a mold/with the silicone layers against each other directly. For purposes of this Example 1 and the testing thereof that follows, a commercially available silicone bathtub caulk was used, which was found not to irritate the wearer's skin during several nightly uses. However, it is preferred that a biocompatible, medically-approved silicone elastomer be chosen for use, as identified below.

Example 2

Silicone on Fleeced Side

The SSM is laid out with the outer woven side facing down and the inner fleeced side facing up. The material is slightly stretched so when applying the silicon elastomer layer to the upwardly-facing fleece side, the SSM will not bunch up when applied using the apparatus described herein. Thickness of the silicone should be adjusted as desired to meet overall process parameters. The silicone material was applied manually via tube using a roller, while allowing a slight build-up in front of the roller. Caution was exercised not to impregnate the silicone material through the soft SSM fleece side. Light pressure only was used. See FIGS. 11-12.

As mentioned above, it is preferred that suitably rated biocompatible, hypoallergenic silicone compounds be commercially utilized. Such silicone materials that are clear and heat curable are available from Momentive, Inc., of Columbus, Ohio. These materials include a paste formulation denoted RTV108 which carries NSF, FDA 21 CFR 177.2600 certification, and is compliant with USP Class VI testing, which is spreadable with a roller as taught herein. Also suitable is RTV118, also from Momentive, Inc., which is a flowable, self-leveling liquid and carries NSF, FDA 21 CFR 177.2600 certification, and is compliant with USP Class VI testing. Those skilled in the art will appreciate the process parameters that differ as between the spreadable paste and flowable, self-leveling liquid silicone materials denoted immediately above. There are graduated viscosities further possible, as will be appreciated by those reasonably skilled in the art. Momentive Data Sheets RTV118 and RTV 108 are provided herewith and expressly incorporated by reference and relied-upon herein.

Physical properties of the laminar composite body (14, 114, 214, 314, 414) according to the present invention were measured using a Taber Stiffness Tester Model 150E, manufactured by Taber Industries of Tonawanda, N.Y. and shown by a photograph of that equipment in FIG. 41. This is believed to yield more concise results as opposed to testing on the Taber Model 112 Fabric Stiffness Tester, also made by the afore-mentioned Taber Industries.

Tested were a total of fifteen (15) specimens made according to the present body (14, 114, 214, 314, 414). Instrument set-up was as follows. Instrument used was a Taber Stiffness Tester—Model 150E having a measuring Range within so-called 'Range 2' (0 to 10 Taber Stiffness Units). Deflection was 15 degrees. This equipment is intended by the manufacturer to measure materials in so-called "Range 2", i.e., between 0 to 10 Taber Stiffness Units ("TSU"). To test in 'Range 2', specimens were cut into 1.5 inch squares. These specimens were laid out as can be seen in FIG. 42 and cut to size using shears as the specimens did not cut completely through using the Taber Model 250 'Triple Cut Specimen Shear'. Specimens A through H were tested in the length of the sample and specimens 'I' through 'O' were tested in the width of the sample. The arrows always pointed "down" when actually tested. A representative swatch of the laminate constituting Applicant's cushion was fabricated with approximate dimensions of 4 inches wide by 8 inches long. This sample was then prepared for analysis by cutting with shears into 1.5 inch square specimens, laid out as seen in the photograph in FIG. 42. Each specimen denoted 'A' through 'H' was tested along its length and each specimen denoted 'I' through 'O' was tested along its width, respectively. The arrows pointed "down" when actually tested. The results from testing these swatches are indicated by the arrows on the photo in FIG. 42 and the data are reported in TABLE 1. As will be apparent from TABLE 1, the Taber Stiffness values measured range from about 4 to about 10 Taber Stiffness Units.

TABLE 1

| Specimen | Left | Average | Right | | |
|---|---|---|---|---|---|
| A | 7.57 | 8.13 | 8.7 | | |
| B | 7.96 | 8.93 | 9.9 | | |
| C | 8.42 | 8.61 | 8.8 | | |
| D | 7.58 | 8.74 | 9.9 | | |
| E | 7.38 | 8.64 | 9.9 | | |
| F | 4.94 | 6.34 | 7.7 | | |
| G | 5.22 | 6.42 | 7.6 | Total Average | 7.76 |
| H | 5.43 | 6.61 | 7.8 | Std. Dev. | 1.2 |
| I | 5.33 | 6.41 | 7.5 | | |

TABLE 1-continued

| Specimen | Left | Average | Right | | |
|---|---|---|---|---|---|
| J | 5.85 | 6.19 | 6.53 | | |
| K | 4.51 | 5.77 | 7.02 | | |
| L | 3.97 | 5.21 | 6.46 | | |
| M | 5.44 | 6.16 | 6.88 | | |
| N | 5.28 | 6.87 | 8.46 | Total Average | 6.12 |
| O | 4.9 | 6.25 | 7.61 | Std. Dev. | 0.5 |

A further alternative embodiment of Applicant's invention will now be described. The silicone used in layer(s) 32, previously discussed in conjunction with laminate (14) of FIGS. 5A-5B, may be replaced with a different biocompatible polymer, e.g., a thermoplastic polyvinyl chloride (PVC) deployed as a film from roll stock or other form. Such an alternative has advantages in terms of a considerably more rapid cure time thus lower processing costs, as well as lower material acquisition pricing, versus silicones. Another advantage of this material substitution, besides process simplification, is a potentially less complicated product design with respect to the laminar composition shown by FIGS. 5A-5B. The processing of PVC (and other similar materials) could be done using lamination fixture 570 of FIGS. 13, 14A, 14B and 15 to bond such polymeric material in film form to one or more of fibrous layers 28, 30. The resulting laminate (14) would then be used in the molding operations described by FIGS. 24A-24B, 25A-C. Besides substitution of, e.g., PVC, for silicones, it is made possible to eliminate one of the fibrous layers 28 or 30 (FIGS. 5A-5B) thus having PVC film as a barrier (instead of silicone layers 32) and one of the fibrous layers 28 or 30 laminated together. An adhesive may be used to initially attach the PVC film and fibrous layer(s) 28 or 30 together, which may be sprayed on the PVC prior to locking in place along the frame 574 by mechanism 572.

An alternative approach to the trim fixtures described in FIGS. 27-40 would be to utilize laser-cutting equipment (not shown) to post-form the molded blank. For example, a small $CO_2$ laser having a 200 Watt emitter could be employed, together with scanner coupled directly to the laser optics to gauge different sizes of product blanks to be obtained.

The foregoing description and accompanying drawings illustrate the principles, preferred embodiments and modes of operation of the invention. These should be regarded as illustrative rather than restrictive. However, the invention should not be construed as being limited to the particular embodiments discussed above. Additional variations of the embodiments will be appreciated by those skilled in the art without departing from the scope of the invention as defined by the following claims.

The invention claimed is:

1. A cushion for a patient breathing mask interface device, the cushion comprising: an open body formed into a three-dimensional J-shaped cross section with an interface coupling front portion and a patient contacting back portion, the back portion defining an inboard curl leading into a dampening chamber in fluid communication with a source of a dampening medium, the chamber being juxtaposed with one or more of the patient's airways, wherein the patient contacting portion has a fibrous, slip-resistant surface and an integral fluid impermeable barrier stretch-bonded together into a substantially shape-retaining and dimensionally stable construction.

2. The cushion of claim 1 wherein the body exhibits flexibility between about 4 to about 10 Taber Stiffness Units.

3. The cushion of claim 1 wherein the fibrous, slip resistant surface further comprises a fibrous layer and a sealing layer stretch-bonded together into a laminar composite.

4. The cushion of claim 1 wherein the body further comprises a nosepiece having an open, generally triangular profile with the inboard curl surrounding the nose of the patient.

5. The cushion of claim 1 wherein the body further comprises a nose pillows.

6. The cushion of claim 1 further comprising a full face cushion wherein the body defines an open generally triangular profile with the inboard curl surrounding the nose and mouth of the patient.

7. The cushion of claim 1 wherein the fibrous, slip-resistant surface further comprises a woven puffy fabric.

8. The cushion of claim 1 wherein the fluid impermeable barrier further comprises an elastomeric sealing layer.

9. The cushion of claim 7 wherein the body further comprises a plurality of woven fabric layers and one or more sealant layers.

10. The cushion of claim 1 wherein the fibrous surface and fluid impermeable barrier further comprise a stretch-bonded laminar molded composite.

11. A cushion for a patient breathing mask interface, comprising:
a first fibrous mask side layer;
a second slip-resistant fibrous facial side layer, superposed on the first layer;
a third, fluid barrier layer interposed between the first and second layers, the layers having a generally polygonal shape; and
wherein the layers are integrally bonded together into a laminar composite defining a form-fitting, generally self-adjusting three-dimensional body having a J-shaped cross section including an inboard curl defining a patient-engaging portion and an interface-engaging portion, the curl opening into a dampening chamber juxtaposed with one or more of the patient's airways and communicating with a pressurized source of a dampening medium delivered to the chamber, the laminar composite is stretch-bonded together into a substantially shape-retaining and dimensionally-stable construction.

12. The cushion of claim 11 wherein either of the first fibrous mask side layer and second slip-resistant facial side layer is a woven fabric.

13. The cushion of claim 12 wherein either of the first fibrous mask side layer and second slip-resistant facial side layer is a fleeced fabric having a knit surface and a puffy brushed body-side surface.

14. The cushion of claim 12 wherein the first fibrous mask side layer is a fleeced fabric and the third layer is an elastomeric sealant, the composite further comprising a stretch-bonded laminate.

15. The cushion of claim 14 wherein the knit surface of the first fibrous mask side layer is in contact with the third fluid barrier layer.

16. The cushion of claim 14 wherein the puffy surface of the first layer is in contact with the patient's face.

17. The cushion of claim 12 wherein the second slip-resistant facial side layer is a fleeced fabric.

18. The cushion of claim 17 wherein the second slip-resistant facial side layer has a puffy brushed surface.

19. The cushion of claim 18 wherein the knit surface of the second slip-resistant facial side layer is in contact with the third fluid barrier layer.

20. The cushion of claim 11 wherein both of the first and second layers are a woven fabric.

21. The cushion of claim 11 wherein the first fibrous mask side layer and second slip-resistant facial side layer are each a fleeced fabric having a knit surface and a puffy brushed surface, with the knit surfaces of each layer being in contact with the third, fluid barrier layer.

22. The cushion of claim 11 wherein the cushion is part of a nosepiece for a Continuous Positive Air Pressure mask, which covers the nasal airway of the patient.

23. The cushion of claim 11 wherein the cushion covers airways of both the nose and mouth of the patient.

24. The cushion of claim 11 wherein the cushion covers the nasal airway of the patient.

25. The cushion of claim 11, adapted for a Continuous Positive Air Pressure patient mask interface, the barrier further comprising an elastomeric sealing third, fluid barrier layer, wherein the laminar composite body has a form-fitting, generally self-adjusting three-dimensional shape defining an air chamber communicating with a pressurized air source, the inboard curl opening into the chamber adjacent one of the patient's airways, and wherein the laminar composite is stretch-bonded together into a substantially shape-retaining construction.

26. The cushion of claim 11 further comprising patient nose pillows for a Continuous Positive Air Pressure mask interface.

27. A method of making a cushion blank for a patient breathing mask interface, the method comprising the steps of:
    (a) providing a mold set having a first platen with a generally annular protruding wall including inner and outer surfaces terminating in a common lip and a juxtaposed second platen including a corresponding generally annular groove, the lip and groove together confining a mold space as the platens are moved relative to one another;
    (b) providing a stretchable laminar composite sheet having a fibrous surface and a fluid impermeable barrier;
    (c) providing a means for retaining the sheet of (b) in fixed position between the lip and groove;
    (d) relatively moving the platens and entrapping the sheet in tension within the mold space as the mold set is closed; and
    (e) opening the mold set and removing a three-dimensional form-fitting, generally self-adjusting cushion blank having a curled lip, the composite sheet of the blank exhibiting a Taber Stiffness value between about 4 to about 10 Taber Stiffness Units.

28. The method of claim 27 further comprising the step of: providing a woven second layer of step (b), including a knit surface and an opposite puffy brushed surface.

29. The method of claim 28 further comprising the step of: applying an elastomeric sealing layer of step (c) to the knit surface of the second layer.

30. The method of claim 28 further comprising the step of: providing a woven first layer of step (c) including a knit surface and an opposite puffy brushed surface.

31. The method of claim 30 further comprising the step of: applying the elastomer of step (c) to the knit side of each of the first and second fibrous layers.

32. The method of claim 31 further comprising the step of: applying a flowable, self-leveling silicone elastomer to either of the first and second layers.

33. The method of claim 31 further comprising the step of: applying a spreadable silicone elastomer paste to each of the first and second layers.

34. The method of claim 30 further comprising the step of: applying the elastomer of step (c) to the puffy brushed side of each of the first and second fibrous layers.

35. The method of claim 27 further comprising the step of: applying a flowable, self-leveling silicone elastomer to either of the first and second layers.

36. The method of claim 35 further comprising the step of: applying the flowable; self-leveling silicone elastomer to both of the first and second layers, respectively.

37. The method of claim 27 further comprising the step of: applying a spreadable silicone elastomer paste to at least one of the first and second layers.

38. The method of claim 37 further comprising the step of: applying a spreadable silicone elastomer paste to each of the first and second layers.

39. The method of claim 27 wherein the retaining means of steps (c) further comprises a tambour ring having an inner annular surface that slides over the sheet of step (b) and the outer surface of the wall of step (a) thereby stretching and entrapping the sheet in the mold space as the platens are relatively moved.

40. An interface for a Continuous Positive Air Pressure mask having a contoured nose portion, the interface comprising:
    (a) a bracket mounted to the mask adjacent the nose portion;
    (b) a cushion supported by a flange articulating with the bracket, the cushion including (i) a first fibrous mask side layer, (ii) a second slip-resistant fibrous facial side layer, superposed on the first layer, and (iii) a third, elastomeric sealing layer interposed between the first and second layers, the layers having an open generally triangular shape; and
    (c) wherein the layers are stretch-bonded together into an integral laminar composite defining a form-fitting, generally self-adjusting open, dimensionally-constant triangular shaped body containing an air chamber juxtaposed with the patient's nasal airway and communicating with a pressurized air source, the body further having a J-shaped cross section including an inboard curl that engages the bridge of the patient's nose and facial curves, the body also including a contiguous outboard wall that terminates in a mask engaging rim, the laminar composite is stretch-bonded together into a substantially shape-retaining construction.

41. The cushion of claim 1 wherein the slip-resistant surface includes a single fibrous layer and a single film barrier layer stretch-bonded together to form the body.

* * * * *